(12) United States Patent
Forbes et al.

(10) Patent No.: US 11,785,702 B2
(45) Date of Patent: Oct. 10, 2023

(54) METHOD AND SYSTEM FOR REMOTE MONITORING OF PROTON BEAM EMITTING AND DELIVERY SYSTEMS

(71) Applicant: VARIAN MEDICAL SYSTEMS, INC., Palo Alto, CA (US)

(72) Inventors: Brian Forbes, Palo Alto, CA (US); Joel Rumley, Palo Alto, CA (US); Imran Tariq, Palo Alto, CA (US); Eric Grossimon, Palo Alto, CA (US); Brian Morse, Palo Alto, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/885,358

(22) Filed: Aug. 10, 2022

(65) Prior Publication Data

US 2022/0386446 A1    Dec. 1, 2022

Related U.S. Application Data

(63) Continuation of application No. 17/327,480, filed on May 21, 2021, now Pat. No. 11,445,594.

(51) Int. Cl.
*A61N 5/10* (2006.01)
*H05H 7/00* (2006.01)

(52) U.S. Cl.
CPC ............... *H05H 7/00* (2013.01); *A61N 5/10* (2013.01); *A61N 2005/1088* (2013.01); *H05H 2277/113* (2013.01)

(58) Field of Classification Search
None
See application file for complete search history.

(56) References Cited

U.S. PATENT DOCUMENTS

| 5,585,642 A | 12/1996 | Britton et al. |
| 11,445,594 B1* | 9/2022 | Forbes ..................... A61N 5/10 |
| 2004/0200982 A1* | 10/2004 | Moriyama ........... A61N 5/1079 |
| | | 250/492.3 |

(Continued)

OTHER PUBLICATIONS

Notice of Allowance on U.S. Appl. No. 17/327,480 dated May 11, 2022.

(Continued)

*Primary Examiner* — Hoon K Song
(74) *Attorney, Agent, or Firm* — FOLEY & LARDNER LLP

(57) ABSTRACT

A remote diagnostic monitoring of operating states for physical components of a particle accelerator system includes generating, by at least one processor, a component hierarchy corresponding to a physical arrangement of one or more physical components of a particle emitting system and including corresponding operating indicators of operating states of the physical components, identifying, by the at least one processor, a faulted physical component among the physical components, identifying, by the at least one processor, one or more fault path components among the physical components, the fault path components corresponding to a portion of the physical arrangement associated with the faulted physical component, and modifying, by the at least one processor, the operating indicators of the fault path components to fault state indicators.

20 Claims, 20 Drawing Sheets

(56) References Cited

U.S. PATENT DOCUMENTS

| | | |
|---|---|---|
| 2010/0303205 A1 | 12/2010 | Kapoor et al. |
| 2014/0037063 A1 | 2/2014 | Gertner et al. |
| 2018/0085603 A1 | 3/2018 | Kruesi et al. |
| 2018/0093110 A1 | 4/2018 | Berlinger et al. |
| 2018/0243584 A1 | 8/2018 | Nord et al. |

OTHER PUBLICATIONS

EPO Search Report on EP Application No. 22173544 dated Sep. 29, 2022 (9 pages).

\* cited by examiner

500

- Operating System 510
- Component State Engine 520
  - Component State Processor 522
  - Component Interlock Processor 524
- Component Topology Engine 530
  - Hierarchy Processing Engine 532
  - Schematic Processing Engine 534
- Control Authorization Engine 540
  - Authorization Input Engine 542
- Network Interface Engine 550
  - Interconnect Interface Controller 552
  - Control Interface Controller 554
  - Monitor Interface Controller 556
- Device Command Processor 560
- Interconnect Command Translator 562

| | |
|---|---|
| Operating System 710 | Presentation Engine 740 |
| Interface Input Engine 720 | Hierarchy Presentation Engine 742 |
| Network Interface Engine 730 | Schematic Presentation Engine 744 |
| Control Interface Controller 732 | Interlock Presentation Controller 746 |
| Monitor Interface Controller 734 | User Presentation Controller 748 |

| Delivery System Report | 810 | Imager Report | 830 | Gantry Actuator Report | 850 |
| --- | --- | --- | --- | --- | --- |
| Software Version | | Orientation State | | Orientation State | |
| Delivery Facility State | | Position 1 Configuration State | | ☑ Actuator Interlock 1 | |
| Robot State | | Position 2 Configuration State | | ☑ Actuator Interlock 2 | |
| System Temperature | | ☑ Imager Interlock 1 | | ☑ Actuator Interlock 3 | |
| System Overview Report 820 | | ☑ Imager Interlock 2 | | ☑ Actuator Interlock 4 | |
| ☑ Sys. Interlock 1 | | ☑ Imager Interlock 3 | | | |
| ☑ Sys. Interlock 2 | | Scanning/Eye Nozzle Report | 840 | Table/Chair Actuator Report | 860 |
| ☑ Sys. Interlock 3 | | Orientation State | | Orientation State | |
| ☑ Sys. Interlock 4 | | ☑ Noz. Interlock 1   ☑ ☑ | | ☑ Actuator Interlock 1 | |
| ☑ Sys. Interlock 5 | | ☑ Noz. Interlock 2  ☑ ☑ ☑ | | ☑ Actuator Interlock 2 | |
| ☑ Sys. Interlock 6 | | ☑ Noz. Interlock 3   ☑ ← 842 | | ☑ Actuator Interlock 3 | |
| ☑ Sys. Interlock 7 | | ☑ Noz. Interlock 4 | | ☑ Actuator Interlock 4 | |

Fig. 8

```
                                                                    1200
┌─────────────────────────────────────────────────────────────┐
│   Obtain Operating State(s) of Particle System Component(s)  1210
│   ┌───────────────────────────────────────────────────────┐ │
│   │   Obtain from Component(s) at Remote Physical Site(s) │ │
│   │                                                   1212│ │
│   └───────────────────────────────────────────────────────┘ │
└─────────────────────────────────────────────────────────────┘
                             ↓
┌─────────────────────────────────────────────────────────────┐
│   Associate Operating State(s) with Operating Indicator(s)   │
│                                                         1220 │
└─────────────────────────────────────────────────────────────┘
                             ↓
┌─────────────────────────────────────────────────────────────┐
│       Generate Component Hierarchy for Component(s)    1230  │
│   ┌───────────────────────────────────────────────────────┐ │
│   │     Generate for Physical Arrangement of Component(s) │ │
│   │                                                   1232│ │
│   └───────────────────────────────────────────────────────┘ │
│   ┌───────────────────────────────────────────────────────┐ │
│   │           Generate with Operating Indicator(s)        │ │
│   │                                                   1234│ │
│   └───────────────────────────────────────────────────────┘ │
└─────────────────────────────────────────────────────────────┘
                             ↓
┌─────────────────────────────────────────────────────────────┐
│     Obtain System Interlock Template (SIT) for Component(s)  1240
│   ┌───────────────────────────────────────────────────────┐ │
│   │       Obtain SIT with Fault Tolerance Criterion/a     │ │
│   │                                                   1242│ │
│   └───────────────────────────────────────────────────────┘ │
└─────────────────────────────────────────────────────────────┘
                             ↓
┌─────────────────────────────────────────────────────────────┐
│   Identify Faulted Physical Component(s) from Component(s) 1250
│   ┌───────────────────────────────────────────────────────┐ │
│   │   Identify Device for Faulted Physical Component(s) (FPC)
│   │                                                   1252│ │──→ ( 1302 )
│   └───────────────────────────────────────────────────────┘ │
│   ┌───────────────────────────────────────────────────────┐ │
│   │      Identify Device by Fault Tolerance Criterion/a   │ │
│   │                                                   1254│ │
│   └───────────────────────────────────────────────────────┘ │
└─────────────────────────────────────────────────────────────┘
```

Generate Operating State Indicator(s) from Operating State(s) 1510

Present Fault Control Interface with Control Affordance(s) 1520

Present Control Affordance for Remote Component(s) 1522

Present with Faulted Component Presentation Portion 1524

Present Arrangement Presentation with Component(s) 1530

Present with Interlock including Component(s) 1532

Present with Operating State Indicator for Component(s) 1534

Present with Operating State Indicator for Interlock 1536

Poll for Control Authorization Instruction 1540

Poll Remote Site for Control Authorization Instruction 1542

Receive Control Affordance Activation Indication(s) 1550

Generate Device Command for Component(s) 1560 → 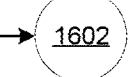 1602

Fig. 15

```
┌─────────────────────────────────────────────────────────────┐
│  Initialize Component(s) at Clinical Site          1910     │
│  ┌───────────────────────────────────────────────────────┐  │
│  │ Initialize Proton Beam Emitting System Component(s)   │  │
│  │                                                  1912 │  │
│  └───────────────────────────────────────────────────────┘  │
│  ┌───────────────────────────────────────────────────────┐  │
│  │ Initialize Proton Beam Delivery System Component(s)   │  │
│  │                                                  1914 │  │
│  └───────────────────────────────────────────────────────┘  │
│  ┌───────────────────────────────────────────────────────┐  │
│  │ Initialize Proton Beam Gateway System Component(s)    │  │
│  │                                                  1916 │  │
│  └───────────────────────────────────────────────────────┘  │
└─────────────────────────────────────────────────────────────┘
                              ↓
┌─────────────────────────────────────────────────────────────┐
│  Detect Component(s) at Clinical Site              1920     │
│  ┌───────────────────────────────────────────────────────┐  │
│  │ Detect at Clinical Site Remote from Technician Site   │  │
│  │                                                  1922 │  │
│  └───────────────────────────────────────────────────────┘  │
│  ┌───────────────────────────────────────────────────────┐  │
│  │ Detect from Component(s) of Proton Emitting System    │  │
│  │                                                  1924 │  │
│  └───────────────────────────────────────────────────────┘  │
│  ┌───────────────────────────────────────────────────────┐  │
│  │ Detect from Component(s) of Proton Delivery System    │  │
│  │                                                  1926 │  │
│  └───────────────────────────────────────────────────────┘  │
└─────────────────────────────────────────────────────────────┘
                              ↓
┌─────────────────────────────────────────────────────────────┐
│  Interrogate Component(s) for Operating State(s)   1930     │
│  ┌───────────────────────────────────────────────────────┐  │
│  │ Interrogate Proton Beam Emitting System Component(s)  │  │
│  │                                                  1932 │  │
│  └───────────────────────────────────────────────────────┘  │
│  ┌───────────────────────────────────────────────────────┐  │
│  │ Interrogate Proton Beam Delivery System Component(s)  │  │
│  │                                                  1934 │  │
│  └───────────────────────────────────────────────────────┘  │
└─────────────────────────────────────────────────────────────┘
                              ↓
                           ( 2002 )
```

METHOD AND SYSTEM FOR REMOTE MONITORING OF PROTON BEAM EMITTING AND DELIVERY SYSTEMS

CROSS-REFERENCE TO RELATED PATENT APPLICATIONS

This application claims the benefit of priority under 35 U.S.C. § 120 as a continuation of U.S. patent application Ser. No. 17/327,480, filed May 21, 2021, the contents of such application being hereby incorporated by reference in its entirety and for all purposes as if completely and fully set forth herein.

TECHNICAL FIELD

The present implementations relate generally to radiation therapy, and more particularly to remote monitoring of proton beam emitting and delivery systems.

BACKGROUND

Radiation therapy is becoming increasingly desired in the treatment of medical conditions and illnesses. Radiation therapy systems capable of concurrently treating multiple patients efficiently and effectively are also becoming increasingly desired. Control and monitoring of radiation therapy is thus becoming increasingly complex, and includes increasingly complex systems and devices in order to provide sufficient breadth of treatment to sufficient number of patients at increasing aggregate volume. Accordingly, maintaining operation of radiation therapy systems is increasingly complex. Conventional radiation therapy systems require increasingly complex servicing and control of components of those system. Such servicing of convention systems requires on-site servicing by technicians that can reduce system uptime and increase delay in critical medical care.

Conventional on-site servicing of proton beam therapy system requires significant monitoring and control service equipment co-located with each proton beam therapy system. Each servicing center requires control and operation by technician staff, often requiring around-the-clock presence of trained technician teams co-located with each deployed proton beam therapy system in order to ensure safe and reliable operation. With the deployment of increasing numbers of proton beam therapy systems across geographic boundaries, the high cost of installation and operations of co-located service equipment increases significantly and requires significant numbers of technicians within limited geographical range of each proton beam therapy system deployed. Thus, cost and complexity of servicing proton beam therapy systems can dramatically increase overall difficulty in deploying and operating critical medical treatments with proton beam therapy.

SUMMARY

To overcome the above and other issues, present implementations are directed to remote monitoring of proton beam emitting and delivery systems. Present implementations can reduce the number of co-located technicians and service monitoring equipment required to perform monitoring of proton beam emitting and delivery systems, allowing proton beam emitting and delivery systems to be deployed at significantly more locations while reducing the infrastructure requirements and cost burdens associated with co-locating large staffs of technicians with at each proton beam emitting and delivery system location. Present implementations include multiple hardware interconnects operatively couplable to specific hardware components of proton beam emitting and delivery systems. These interconnects provide a technical solution for allowing servicing technicians to remotely monitor proton beam emitting and delivery systems, and to diagnose operating faults without the requirement to be co-located with the proton beam emitting and delivery system location. Further, present implementations include a dedicated communication channel for monitoring proton beam emitting and delivery systems, within a network infrastructure operatively couplable to components of proton beam emitting and delivery systems. Present implementations further monitor and control operating states of one or more components of proton beam emitting and delivery systems directly, to conduct servicing, troubleshooting, or the like. Thus, a technological solution for remote control and remote monitoring of proton beam emitting and delivery systems is provided.

Example implementations include a method for remote diagnostic monitoring of operating states for physical components of a particle accelerator system, the method including obtaining, by at least one processor at a first physical location, one or more operating states corresponding to one or more physical components associated with a particle emitting system and a particle delivery system each located at a second physical location remote from the first physical location, associating, by the at least one processor, the operating states with corresponding operating indicators, generating, by the at least one processor, a component hierarchy corresponding to a physical arrangement of the physical components of the particle emitting system and including the corresponding operating indicators, identifying, by the at least one processor, a faulted physical component among the physical components, identifying, by the at least one processor, one or more fault path components among the physical components, the fault path components corresponding to a portion of the physical arrangement associated with the faulted physical component, modifying, by the at least one processor, the operating indicators of the fault path components to fault state indicators, and presenting, by the at least one processor, a fault monitor presentation including the operating indicators and a faulted component presentation portion corresponding to the fault state indicators.

Example implementations also include a method of further generating a hierarchical presentation including at least the portion of the physical arrangement associated with the faulted physical component.

Example implementations also include a method where the physical arrangement corresponds to at least one physical device including at least one included physical component among the physical components, and the hierarchical presentation includes at least one of the physical device and the included physical component in accordance with a monitor access criterion.

Example implementations also include a method where the monitor access criterion corresponds to a first access criterion, and the hierarchical presentation includes the physical device and the included physical component.

Example implementations also include a method where the monitor access criterion corresponds to a second access criterion, and the hierarchical presentation includes the physical device and excludes the included physical component.

Example implementations also include a method where the identifying the faulted physical component includes identifying the included physical component, and the identifying the fault path components among the physical components includes identifying the physical device.

Example implementations also include a method where the identifying the physical device includes identifying the physical device in accordance with a fault tolerance criterion associated with the physical device and the included physical component.

Example implementations also include a method of further obtaining, by the at least one processor, a system interlock template corresponding to the physical components associated with one or more of the particle emitting system and the particle delivery system, where the system interlock template includes the fault tolerance criterion.

Example implementations also include a method of further traversing, by the at least one processor, the hierarchical presentation in accordance with the component hierarchy to identify the faulted physical component and one or more of the fault path components.

Example implementations also include a method of further generating a schematic presentation including at least the faulted physical component and at least one physical component operatively coupled to the faulted physical component.

Example implementations also include a user interface system for remote diagnostic monitoring of operating states for physical components of a particle system, with a network interface engine configured to obtain, at a first physical location, one or more operating states corresponding to one or more physical components associated with a particle emitting system and a particle delivery system each located at a second physical location remote from the first physical location, a component state engine configured to associate the operating states with corresponding operating indicators, a hierarchy processing engine configured to generate a component hierarchy corresponding to a physical arrangement of the physical components and including the corresponding operating indicators, identify one or more fault path components among the physical components, the fault path components corresponding to a portion of the physical arrangement associated with the faulted physical component, and modify the operating indicators of the fault path components to fault state indicators, and a presentation engine configured to present a fault monitor presentation including the operating indicators and a faulted component presentation portion corresponding to the fault state indicators.

Example implementations also include a system where the presentation engine includes a hierarchy presentation engine configured to generate a hierarchical presentation including at least the portion of the physical arrangement associated with the faulted physical component, where the fault monitor presentation includes the hierarchical presentation.

Example implementations also include a system where the physical arrangement corresponds to at least one physical device including at least one included physical component among the physical components, and the hierarchical presentation includes at least one of the physical device and the included physical component in accordance with a monitor access criterion.

Example implementations also include a system where the presentation engine further includes an interlock presentation controller configured to selectably present, in accordance with a first access criterion, the hierarchical presentation including the physical device and the included physical component, and to selectably present, in accordance with a second access criterion, the hierarchical presentation including the physical device and excluding the included physical component.

Example implementations also include a system where the hierarchy processing engine is further configured to identify the faulted physical component by identifying the included physical component, and identify the fault path components among the physical components by identifying the physical device.

Example implementations also include a system where the hierarchy processing engine is further configured to identify the physical device in accordance with a fault tolerance criterion associated with the physical device and the included physical component.

Example implementations also include a system with a network interface operatively coupled to the particle emitting system and the particle delivery system, and configured to obtain a system interlock template corresponding to the physical components associated with the particle emitting system and the particle delivery system, where the system interlock template includes the fault tolerance criterion.

Example implementations also include a system where the presentation engine includes a schematic presentation engine configured to generate a schematic presentation including at least the faulted physical component and at least one physical component operatively coupled to the faulted physical component, where the fault monitor presentation includes the schematic presentation.

Example implementations also include a computer system with a processor in communication by a network interface with physical components of a particle accelerator system, the processor configured to obtain one or more operating states corresponding to one or more physical components associated with a particle emitting system and a particle delivery system each located at a second physical location remote from the first physical location, associate the operating states with corresponding operating indicators, generate a component hierarchy corresponding a physical arrangement of the physical components and including the corresponding operating indicators, identify a faulted physical component among the physical components, identify one or more fault path components among the physical components, the fault path components corresponding to a portion of the physical arrangement associated with the faulted physical component, modify the operating indicators of the fault path components to fault state indicators, and present a fault monitor presentation including the operating indicators and a faulted component presentation portion corresponding to the fault state indicators.

Example implementations also include a system where the particle emitting system includes a proton beam cyclotron.

BRIEF DESCRIPTION OF THE DRAWINGS

These and other aspects and features of the present implementations will become apparent to those ordinarily skilled in the art upon review of the following description of specific implementations in conjunction with the accompanying figures, wherein:

FIG. 5 illustrates a system memory, further to the proton beam system gateway of FIG. 2, according to an embodiment.

FIG. 7 illustrates a system memory further to the diagnostic system of FIG. 6, according to an embodiment.

FIG. 8 illustrates a graphical user interface for remote monitoring of a proton beam emitting and delivery system, according to an embodiment.

FIG. 12 illustrates a method of remote monitoring of a proton beam emitting and delivery system, according to an embodiment.

FIG. 15 illustrates a method of remote control of a proton beam emitting and delivery system, according to an embodiment.

FIG. 19 illustrates a method of remote control of a proton beam emitting and delivery system at a clinical location, according to an embodiment.

DETAILED DESCRIPTION

Figure 1:
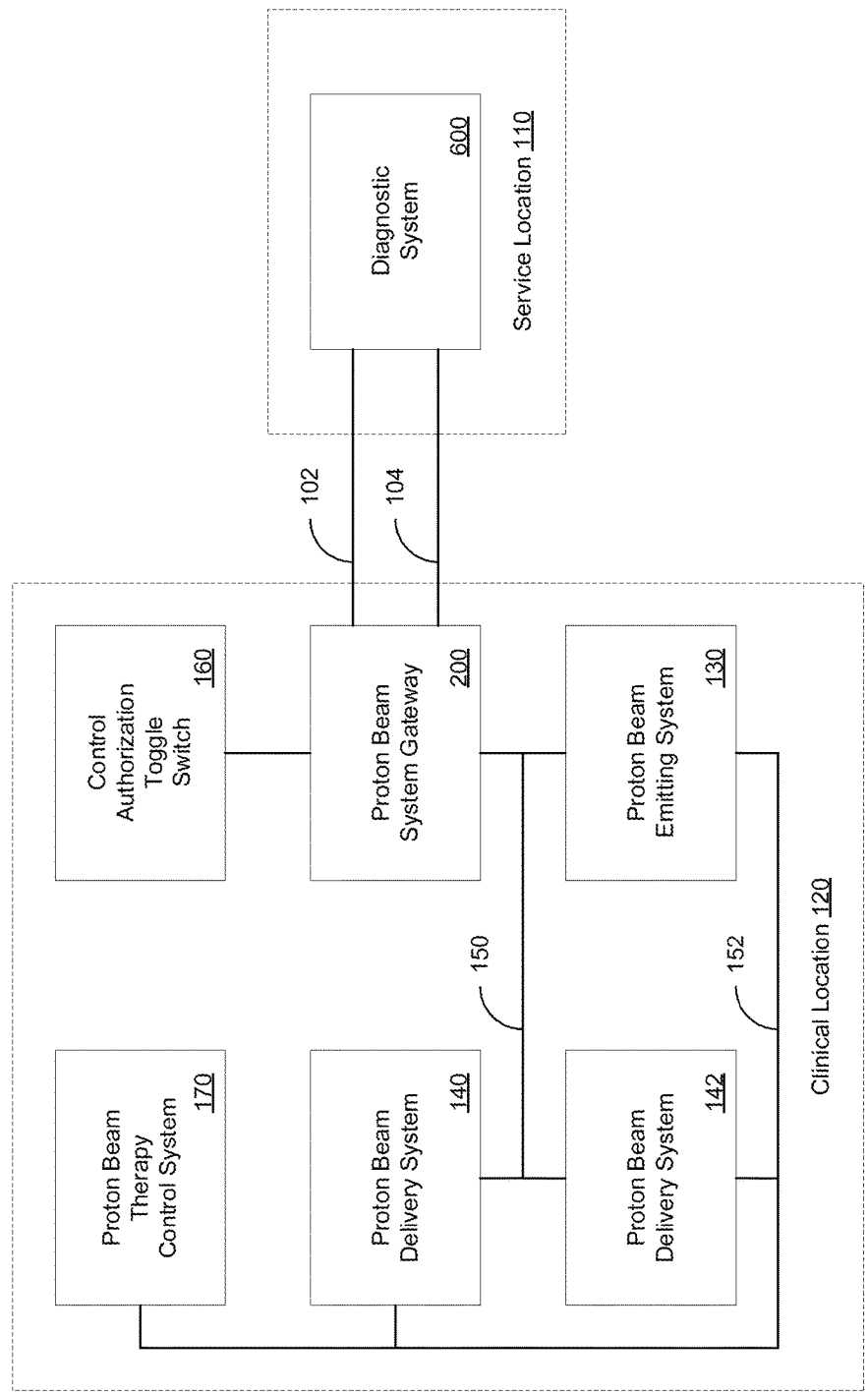
FIG. 1 illustrates a system for remote control and remote monitoring of a proton beam emitting and delivery system, according to an embodiment.

The present implementations will now be described in detail with reference to the drawings, which are provided as illustrative examples of the implementations so as to enable those skilled in the art to practice the implementations and alternatives apparent to those skilled in the art. Notably, the figures and examples below are not meant to limit the scope of the present implementations to a single implementation, but other implementations are possible by way of interchange of some or all of the described or illustrated elements. Moreover, where certain elements of the present implementations can be partially or fully implemented using known components, only those portions of such known components that are necessary for an understanding of the present implementations will be described, and detailed descriptions of other portions of such known components will be omitted so as not to obscure the present implementations. Implementations described as being implemented in software should not be limited thereto, but can include implementations implemented in hardware, or combinations of software and hardware, and vice-versa, as will be apparent to those skilled in the art, unless otherwise specified herein. In the present specification, an implementation showing a singular component should not be considered limiting; rather, the present disclosure is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present implementations encompass present and future known equivalents to the known components referred to herein by way of illustration.

Present implementations are directed variously to hardware interconnects, network infrastructure, and user interfaces for providing a technical solution for remote monitoring of proton beam emitting and delivery systems. First, present implementations include hardware interconnects operatively couplable to specific hardware components of proton beam emitting and delivery systems to monitor the operating state of those hardware components. Thus, implementations in accordance with present implementations can provide direct hardware-level monitoring of components of proton beam emitting and delivery systems, and reduce and eliminate the need of costly co-located technician teams and service equipment. A single diagnostic system can be coupled to an arbitrary number of proton beam emitting and delivery systems at a remote location by a dedicated service communication channel. The service communication channel can be Internet-enabled to allow direct hardware-level monitoring of components of proton beam emitting and delivery systems from any location. Thus, present implementations can enable a technological solution of direct and secure remote monitoring and control of proton beam emitting and delivery system hardware components.

FIG. 1 illustrates an example system for remote control and remote monitoring of a proton beam emitting and delivery system, in accordance with present implementations. As illustrated by way of example in FIG. 1, an example system 100 includes a diagnostic system 600 at a service location 110, and a proton beam emitting system 130, a first proton beam delivery system 140, a second proton beam delivery system 142, a proton beam system gateway 200, a service communication channel 150, an operation communication channel 152, and a control authorization toggle switch 160 at a clinical location 120, a service control channel 102, and a service monitor channel 104.

The service location 110 includes a physical location including a technician site. The service location 110 may correspond to an office, workstation, building, call center, or the like, and includes one or more accommodations for one or more individuals to interact with a diagnostic system. The service location 110 can be located in a particular geographic location, geographic region, geographic jurisdiction, or the like. As one example, a geographic jurisdiction can be a particular city, state town, county, township, country, territory, continent, planetary hemisphere, or the like.

The diagnostic system 600 includes at least one electronic system located at least partially at or within the service location 110, and is operable to receive and transmit one or more instructions from and to the clinical location 120. The diagnostic system 600 may be operatively coupled to the proton beam gateway system 200 by one or more of the service control channel 102 and the service monitor channel 104.

The clinical location 120 includes a physical location including a clinician site. The clinical location 120 may correspond to an office, workstation, building, clinic, hospital, operating room, emergency room, research facility, or the like, and includes one or more accommodations for one or more individuals to interact with the proton beam emitting system 130 and one or more of the proton beam delivery system 140 and 142. The clinical location 120 can be located in a particular geographic location, geographic region, geographic jurisdiction, or the like. As one example, a geographic jurisdiction can be a particular city, state town, county, township, country, territory, continent, planetary hemisphere, or the like. The clinical location 120 can be located at a physical location remote from the service location 110. A first physical location can be remote from a second physical location where the first physical location and the second physical location are located at separate places of corresponding type. As one example, the first physical location can be remotely located from the second physical location where the first physical location is a first building and the second physical location is a second building. In this example, the first and second physical locations can both be located in different buildings within the same or different jurisdictions, states, countries, hemispheres, or the like. As another example, the first physical location can be remotely located from the second physical location where the first physical location is a first city, town, or the like, and the second physical location is a second city, town, or the like. In this example, the first and second physical locations can both be located in different cities, town, or the like within the same or different jurisdictions, states, countries, hemispheres, or the like.

The proton beam emitting system 130 includes a radiation generating system operable to generate directed energy. The proton beam emitting system 130 can be or can include a cyclotron operable to generate one or more focused energy beams including one or more proton beams or the like. The proton beam emitting system 130 can generate at least one proton beam having at least one distribution pattern corresponding to one or more operating states of one or more components thereof or associated therewith. The proton beam emitting system 130 can be operatively coupled to one or more proton beam delivery systems to provide one or more proton beams to the proton beam delivery systems. The proton beam emitting system 130 can be operatively coupled to one or more of the first proton beam delivery system 140 and the second proton beam delivery system 142 by a beam transport system for transmitting a proton beam generated at the proton beam emitting system 130. The proton beam emitting system 130 can be operatively coupled to one or more of the first proton beam delivery system 140 and the second proton beam delivery system 142 by operation communication channel 152 for transmitting instructions to operate the proton beam emitting system 130 in accordance with at least one clinical therapy, proton beam therapy, radiation therapy, or the like.

The first proton beam delivery system 140 is or includes a radiation output system operable to apply directed energy to a target. A target may include a biological organism. As one example, a biological organism can be a person, animal, or the like. As another example, a person can be a patient undergoing a radiation therapy treatment in accordance with directed energy applied from the first proton beam delivery system 140 to at least a portion of a body, body part, or the like, of the patient. The first proton beam delivery system 140 may apply at least one proton beam having at least one distribution pattern corresponding to one or more operating states of one or more components thereof or associated therewith. The first proton beam delivery system 140 may include, correspond to, or be associated with, or the like, a patient treatment room of a medical facility at the clinical location 120. The patient treatment room of the medical facility can correspond to a room, a radiology facility, or the like, of a hospital, medical facility, clinic, or the like.

The first proton beam delivery system 140 may be or may include one or more moveable, articulable, or like components thereof or associated therewith. The first proton beam delivery system 140 can include at least one nozzle including a beam output component. As one example, the nozzle can be a scanning nozzle operable to have a first output characteristic corresponding to a first output aperture for directing a proton beam. As another example, the first output aperture can correspond to a proton beam shape having a size, energy, current, and the like compatible with application of a proton beam to living tissue of a biological organism, patient, and the like. As another example, the nozzle can be an eye nozzle operable to have a second output characteristic corresponding to a second output aperture for directing a proton beam. As another example, the second output aperture can correspond to a proton beam shape having a size, energy, current, and the like compatible with application of a proton beam to living ocular tissue of a biological organism, patient, and the like.

The second proton beam delivery system 142 includes a radiation output system operable to apply directed energy to a target independently of, concurrently, with, or the like, the first proton beam delivery system 140. The second proton beam delivery system 142 can correspond in one or more of structure and operation to the first proton beam delivery system 140. The second proton beam delivery system 142 may include, correspond to, or be associated with, or the like, a patient treatment room of a medical facility at the clinical location 120 and separate from a corresponding patient treatment room of the first proton beam delivery system 140. The clinical location 120 can include an arbitrary number of proton beam delivery systems, and is not limited to the first proton beam delivery system 140 and the second proton beam delivery system 142. Proton beam emitting system 130 can be operatively coupled to an arbitrary number of proton beam delivery systems, and is not limited to being operatively coupled to the first proton beam delivery system 140 and the second proton beam delivery system 142.

The service communication channel 150 is operable to operatively couple one or more of the proton beam emitting system 130, the first proton beam delivery system 140, and the second proton beam delivery system 142 to the proton beam system gateway 200. The service communication channel 150 may be operable to receive and transmit one or more instructions for control and monitoring of the proton beam emitting system 130, the first proton beam delivery system 140, and the second proton beam delivery system 142. The service communication channel 150 may be include one or more digital, analog, or like communication channels, lines, traces, or the like. As one example, the service communication channel 150 is or includes at least one serial or parallel communication line among multiple communication lines of a communication interface. The service communication channel 150 may be or include one or more wireless communication devices, systems, protocols, interfaces, or the like. The service communication channel 150 may include one or more logical or electronic devices including but not limited to integrated circuits, logic gates, flip flops, gate arrays, programmable gate arrays, and the like. The service communication channel 150 may include ones or more telecommunication devices including but not limited to antennas, transceivers, packetizers, wired interface ports, and the like.

The operation communication channel 152 is operable to operatively couple one or more of the proton beam emitting system 130, the first proton beam delivery system 140, and the second proton beam delivery system 142 to a distinct proton beam therapy control system 170. The proton beam therapy control system 170 can be located at least partially at the clinical location 120, can be located at least partially at any location remote from the clinical location, or any combination thereof. The operation communication channel 152 may be operable to receive and transmit one or more instructions for operation of the proton beam emitting system 130, the first proton beam delivery system 140, and the second proton beam delivery system 142 in accordance with one or more clinical therapies, treatments, or the like including application of a proton beam, radiation, or the like. The operation communication channel 152 may correspond in one or more of structure and operation to the service communication channel 150.

The proton beam system gateway 200 includes one or more communication interfaces to operatively couple one or more of the proton beam emitting system 130, the first proton beam delivery system 140, and the second proton beam delivery system 142 to the diagnostic system 600 by one or more of the service control channel 102 and the service monitor channel 104. The proton beam system gateway 200 may be operable to route, mediate, select, switch, or the like, instructions between the diagnostic system 600 and one or more components of the proton beam emitting system 130, the first proton beam delivery system 140, and the second proton beam delivery system 142.

The proton beam system gateway 200 can advantageously interface with the components of one or more of the proton beam emitting system 130, the first proton beam delivery system 140, and the second proton beam delivery system 142 directly, thereby reducing and eliminating failure points in remote service control and remote service monitoring of those systems at the clinical location 120. Thus, the proton beam system gateway 200 can directly receive one or more operating states from components of the proton beam emitting system 130, the first proton beam delivery system 140, and the second proton beam delivery system 142 by a physical, hardware, logical, or like connection thereto. Further, the proton beam system gateway 200 can bypass high-level operating systems, personally identifiable information (PII), personal health information (PHI), and the like, by separating the control and monitoring operations of the proton beam system gateway 200 from clinical operations, therapeutic operations, treatment operations, and the like.

The control authorization toggle switch 160 includes a physical control affordance operable to indicate that the diagnostic system 600 is authorized to execute a control instruction at one or more components of one or more of the proton beam emitting system 130, the first proton beam delivery system 140, and the second proton beam delivery system 142. The control authorization toggle switch 160 may include a button that can be pressed to send an authorization instruction to the proton beam system gateway 200. The control authorization toggle switch 160 may include one or more visual indicators operable to indicate a control authorization state, prompt, or the like. As one example, the control authorization toggle switch 160 can include a green LED, light, or the like disposed within around, proximate to, or the like, the control authorization toggle switch 160, that can indicate that the control authorization toggle switch 160 indicates that the proton beam system gateway 200 is authorized to transmit one or more control instructions. As another example, the control authorization toggle switch 160 can include a red LED, light, or the like disposed within around, proximate to, or the like, the control authorization toggle switch 160, that can indicate that the control authorization toggle switch 160 indicates that the proton beam system gateway 200 is authorized to transmit one or more control instructions. As another example, the control authorization toggle switch 160 can include a pulsating, dimming, brightening, fading, or the like, LED, light, or the like disposed within around, proximate to, or the like, the control authorization toggle switch 160, that can indicate the control authorization toggle switch 160 indicates that the proton beam system gateway 200 is requesting one or more control authorization instructions. The control authorization toggle switch 160 may be stateless and may provide an activation response independent of one or more of a present, previous, or future physical orientation of the control authorization toggle switch 160.

The service control channel 102 is operable to operatively couple the proton beam system gateway 200 to the diagnostic system 600 to transmit one or more instructions therebetween for controlling one or more of the proton beam emitting system 130, the first proton beam delivery system 140, and the second proton beam delivery system 142. The service control channel 102 can advantageously couple the proton beam system gateway 200 to the diagnostic system 600 by a dedicated physical communication channel, logical communication channel, or the like. Thus, the service control channel 102 may be operable to provide secure, dedicated, and stable control communication from a service location 110 to a clinical location 120 for control communications substantially free of interference from monitoring communications. Further, the service control channel 102 may be operable to provide secure, dedicated, and stable control communication from a service location 110 to components of one or more of the proton beam emitting system 130, the first proton beam delivery system 140, and the second proton beam delivery system 142 at a clinical location 120.

The service control channel 102 may include one or more digital, analog, or like communication channels, lines, traces, or the like. As one example, the service control channel 102 is or includes at least one serial or parallel communication line among multiple communication lines of a communication interface. The service control channel 102 may be or may include one or more wireless communication devices, systems, protocols, interfaces, or the like. The service control channel 102 may include one or more logical or electronic devices including but not limited to integrated circuits, logic gates, flip flops, gate arrays, programmable gate arrays, and the like. The service control channel 102 may include ones or more telecommunication devices including but not limited to antennas, transceivers, packetizers, wired interface ports, and the like.

The service monitor channel 104 is operable to operatively couple the proton beam system gateway 200 to the diagnostic system 600 to transmit one or more instructions therebetween for monitoring one or more of the proton beam emitting system 130, the first proton beam delivery system 140, and the second proton beam delivery system 142. The service monitor channel 104 can advantageously couple the proton beam system gateway 200 to the diagnostic system 600 by a dedicated physical communication channel, logical communication channel, or the like. Thus, the service monitor channel 104 may be operable to provide secure, dedicated, and stable control communication from a service location 110 to a clinical location 120 for monitoring communications substantially free of interference from control communications. Further, the service monitor channel 104 may be operable to provide secure, dedicated, and stable control communication from a service location 110 to components of one or more of the proton beam emitting system 130, the first proton beam delivery system 140, and the second proton beam delivery system 142 at a clinical location 120. The service monitor channel 104 can correspond in one or more of structure and operation to the service control channel 102.

Figure 2:
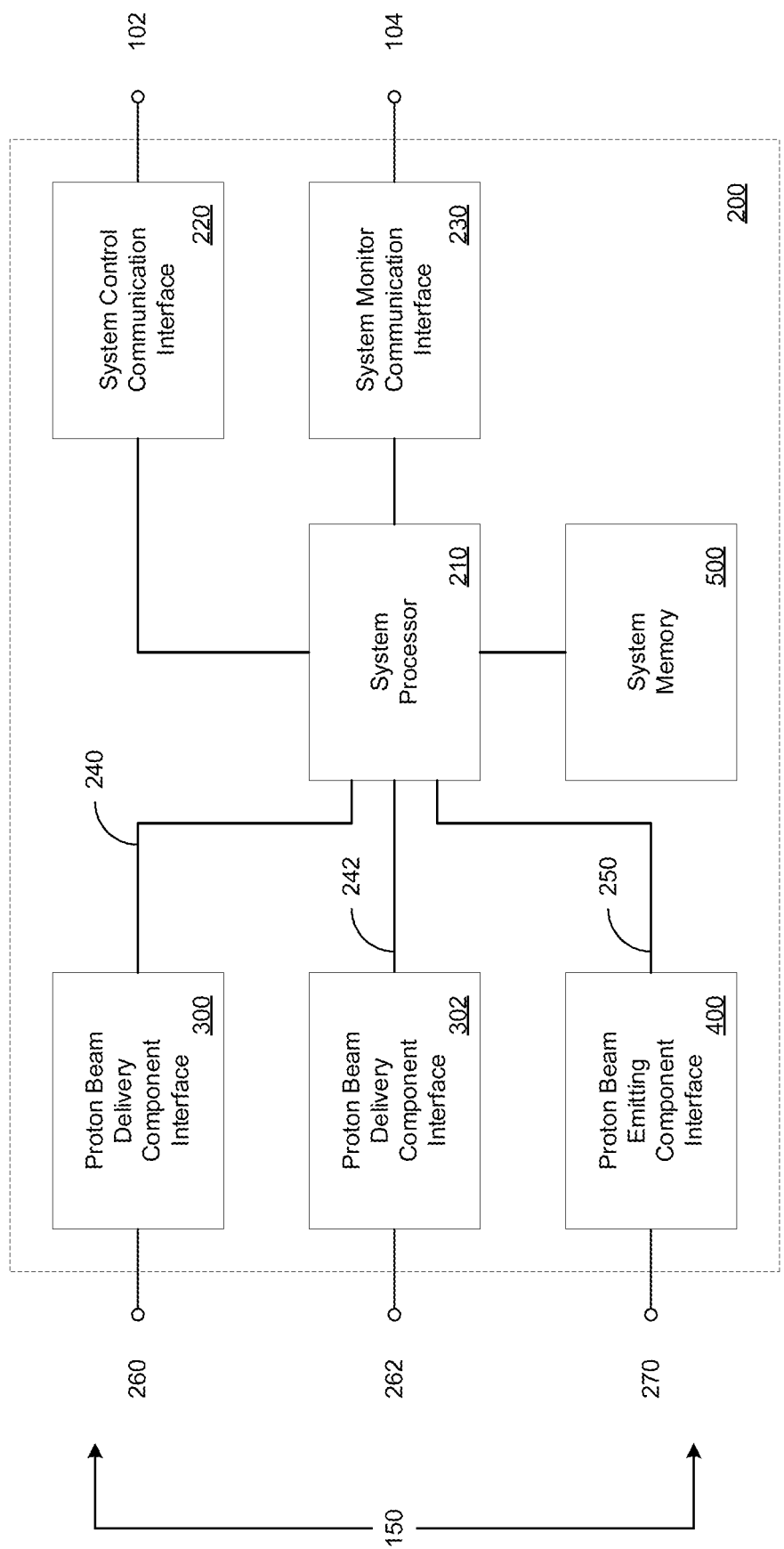
FIG. 2 illustrates a proton beam system gateway, further to the system of FIG. 1, according to an embodiment.

FIG. 2 illustrates an example proton beam system gateway, further to the example system of FIG. 1. As illustrated by way of example in FIG. 2, an example proton beam system gateway 200 includes a system processor 210, a system memory 500, a system control communication interface 220, a system monitor communication interface 230, a first proton beam delivery component interface 300, a second proton beam delivery component interface 302, and a proton beam emitting component interface 400.

The system processor 210 is operable to execute one or more instructions associated with input from the diagnostic system 600. The system processor 210 may be an electronic processor, an integrated circuit, or the like including one or more of digital logic, analog logic, digital sensors, analog sensors, communication buses, volatile memory, nonvolatile memory, and the like. The system processor 210 may include but is not limited to, at least one microcontroller unit (MCU), microprocessor unit (MPU), central processing unit (CPU), graphics processing unit (GPU), physics processing unit (PPU), embedded controller (EC), or the like. The system processor 210 may include a memory operable to store or storing one or more instructions for operating components of the system processor 210 and operating components operably coupled to the system processor 210. The one or more instructions may include at least one of firmware, software, hardware, operating systems, embedded operating systems, and the like. The system processor 210 or the proton beam system gateway 200 generally can include at least one communication bus controller to effect communication between the system processor 210 and the other elements of the proton beam system gateway 200. The system processor 210 includes a first component interface channel 240, a second component interface channel 242, and a third component interface channel 400. The first, second, and third component interface channels 240, 242 and 250 are operable to operatively couple the system processor 210 respectively to the first proton beam delivery component interface 300, the second proton beam delivery component interface 302, and the proton beam emitting component interface 400. One or more of the first, second, and third component interface channels 240, 242 and 250 can be integrated into a combined, single, or like channel.

The system memory 500 is operable to store data associated with the proton beam system gateway 200. The system memory 500 may include ones or more hardware memory devices for storing binary data, digital data, or the like. The system memory 500 may include one or more electrical components, electronic components, programmable electronic components, reprogrammable electronic components, integrated circuits, semiconductor devices, flip flops, arithmetic units, or the like. The system memory 500 may include at least one of a non-volatile memory device, a solid-state memory device, a flash memory device, and a NAND memory device. The system memory 500 may include one or more addressable memory regions disposed on one or more physical memory arrays. A physical memory array may include a NAND gate array disposed on a particular semiconductor device, integrated circuit device, printed circuit board device, and the like.

The system control communication interface 220 is operable to receive and transmit one or more instructions by the service control channel 102 to the diagnostic system 600. The system control communication interface 220 may include a command translation unit operable to convert one or more instructions between a processor format compatible with the system processor 210 and a communication format compatible with one or more of the service control channel 102 and the diagnostic system 600. The system control communication interface 220 may include one or more logical or electronic devices including but not limited to integrated circuits, logic gates, flip flops, gate arrays, programmable gate arrays, and the like. Any electrical, electronic, or like devices, or components associated with the system control communication interface 220 can also be associated with, integrated with, integrable with, replaced by, supplemented by, complemented by, or the like, the system processor 210 or any component thereof.

The system monitor communication interface 230 is operable to receive and transmit one or more instructions by the service monitor channel 104 to the diagnostic system 600. The system monitor communication interface 230 may include a command translation unit operable to convert one or more instructions between a processor format compatible with the system processor 210 and a communication format compatible with one or more of the service monitor channel 104 and the diagnostic system 600. The system monitor communication interface 230 may include one or more logical or electronic devices including but not limited to integrated circuits, logic gates, flip flops, gate arrays, programmable gate arrays, and the like. Any electrical, electronic, or like devices, or components associated with the system monitor communication interface 230 can also be associated with, integrated with, integrable with, replaced by, supplemented by, complemented by, or the like, the system processor 210 or any component thereof.

The first proton beam delivery component interface 300 is operable to receive and transmit one or more instructions by a first proton beam system communication channel 260 of the service communication channel 150 to the first proton beam delivery system 140. The first proton beam delivery component interface 300 may include a command translation unit operable to convert one or more instructions between a processor format compatible with the system processor 210 and a communication format compatible with one or more of the first proton beam system communication channel 260 and the first proton beam delivery system 140.

The first proton beam delivery component interface 300 may include one or more logical or electronic devices including but not limited to integrated circuits, logic gates, flip flops, gate arrays, programmable gate arrays, and the like. Any electrical, electronic, or like devices, or components associated with the first proton beam delivery component interface 300 can also be associated with, integrated with, integrable with, replaced by, supplemented by, complemented by, or the like, the system processor 210 or any component thereof.

The second proton beam delivery component interface 302 is operable to receive and transmit one or more instructions by a second proton beam system communication channel 262 of the service communication channel 150 to the second proton beam delivery system 142. The second proton beam delivery component interface 302 may include a command translation unit operable to convert one or more instructions between a processor format compatible with the system processor 210 and a communication format compatible with one or more of the second proton beam delivery component interface 302 and the second proton beam delivery system 142. The second proton beam delivery component interface 302 may include one or more logical or electronic devices including but not limited to integrated circuits, logic gates, flip flops, gate arrays, programmable gate arrays, and the like. Any electrical, electronic, or like devices, or components associated with the second proton beam delivery component interface 302 can also be associated with, integrated with, integrable with, replaced by, supplemented by, complemented by, or the like, the system processor 210 or any component thereof.

The proton beam emitting component interface 400 is operable to receive and transmit one or more instructions by a third proton beam system communication channel 270 of the service communication channel 150 to the proton beam emitting system 130. The proton beam emitting component interface 400 may include a command translation unit operable to convert one or more instructions between a processor format compatible with the system processor 210 and a communication format compatible with one or more of the proton beam emitting component interface 400 and the proton beam emitting system 130. The proton beam emitting component interface 400 may include one or more logical or electronic devices including but not limited to integrated circuits, logic gates, flip flops, gate arrays, programmable gate arrays, and the like. Any electrical, electronic, or like devices, or components associated with the proton beam emitting component interface 400 can also be associated with, integrated with, integrable with, replaced by, supplemented by, complemented by, or the like, the system processor 210 or any component thereof.

Figure 3:
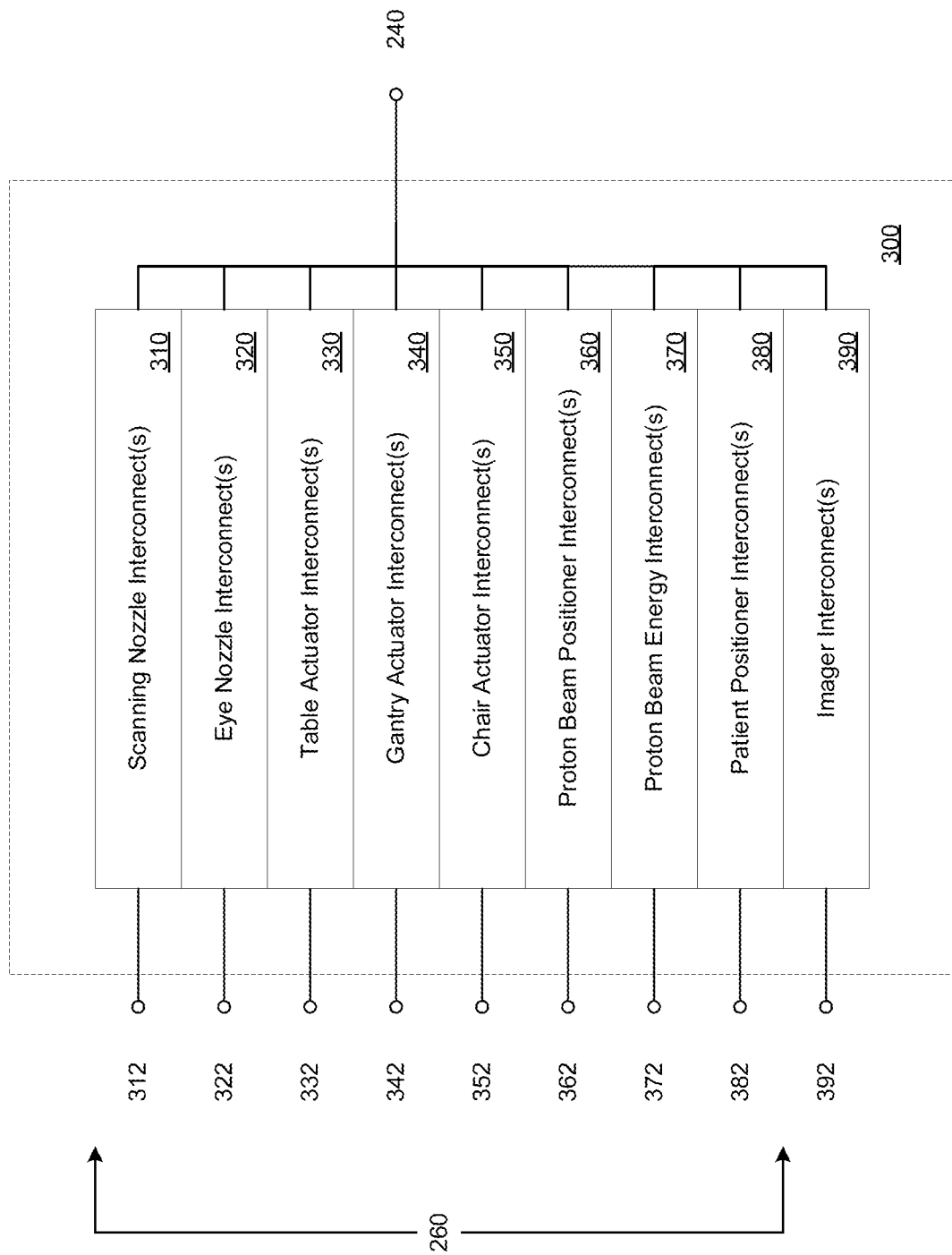
FIG. 3 illustrates a proton beam delivery component interface, further to the proton beam system gateway of FIG. 2, according to an embodiment.

FIG. 3 illustrates an example proton beam delivery component interface, further to the example proton beam system gateway of FIG. 2. As illustrated by way of example in FIG. 3, an example proton beam delivery component interface 300 includes at least one scanning nozzle interconnect 310, at least one eye nozzle interconnect 320, at least one table actuator interconnect 330, at least one gantry actuator interconnect 340, at least one chair actuator interconnect 350, at least one proton beam positioner interconnect 360, at least one proton beam energy interconnect 370, at least one patient positioner interconnect 380, and at least one imager interconnect 390. The proton beam delivery component interface 302 can correspond in one or more of structure and operation to the proton beam delivery component interface 300.

The scanning nozzle interconnect 310 is operable to operatively couple an electrical, electronic, or like component of a scanning nozzle of the proton beam delivery system 140 or 142 respectively to the component interface channel 240 or 242. The scanning nozzle interconnect 310 may include one or more physical control contacts 312 coupled to, integrated with, detachably attached to, or the like, a scanning nozzle of the proton beam delivery system 140 or 142. As one example, the control contacts 312 of the scanning nozzle interconnect 310 can operatively couple the scanning nozzle interconnect 310 to one or more of a power switch, a power reset switch, one or more scanning nozzle positioning motors, one or more scanning nozzle aperture motors, and the like. The scanning nozzle interconnect 310 may include one or more physical monitoring contacts coupled to, integrated with, detachably attached to, or the like, the scanning nozzle of the proton beam delivery system 140 or 142. As one example, the control contacts 312 of the scanning nozzle interconnect 310 can operatively couple the scanning nozzle interconnect 310 to one or more of a component voltage sensor, a component current sensor, one or more scanning nozzle position sensors, one or more scanning nozzle aperture sensors, and the like. The scanning nozzle interconnect 310 may include one or more logical or electronic devices including but not limited to jumper contacts, solder contacts, integrated circuits, logic gates, flip flops, gate arrays, programmable gate arrays, and the like.

The eye nozzle interconnect 320 is operable to operatively couple an electrical, electronic, or like component of an eye nozzle of the proton beam delivery system 140 or 142 respectively to the component interface channel 240 or 242. The eye nozzle interconnect 320 may include one or more physical control contacts 322 coupled to, integrated with, detachably attached to, or the like, an eye nozzle of the proton beam delivery system 140 or 142. As one example, the control contacts 322 of the eye nozzle interconnect 320 can operatively couple the eye nozzle interconnect 320 to one or more of a power switch, a power reset switch, one or more eye nozzle positioning motors, one or more eye nozzle aperture motors, and the like. The eye nozzle interconnect 320 may include one or more physical monitoring contacts coupled to, integrated with, detachably attached to, or the like, the eye nozzle of the proton beam delivery system 140 or 142. As one example, the control contacts 322 of the eye nozzle interconnect 320 can operatively couple the eye nozzle interconnect 320 to one or more of a component voltage sensor, a component current sensor, one or more eye nozzle position sensors, one or more eye nozzle aperture sensors, and the like. The eye nozzle interconnect 320 may include one or more logical or electronic devices including but not limited to jumper contacts, solder contacts, integrated circuits, logic gates, flip flops, gate arrays, programmable gate arrays, and the like.

The table actuator interconnect 330 is operable to operatively couple an electrical, electronic, or like component of at least one table actuator of the proton beam delivery system 140 or 142 respectively to the component interface channel 240 or 242. The table actuator interconnect 330 may include one or more physical control contacts 332 coupled to, integrated with, detachably attached to, or the like, at least one motorized actuator of the proton beam delivery system 140 or 142. As one example, the control contacts 332 of the table actuator interconnect 330 can operatively couple the table actuator interconnect 330 to one or more of a power switch, a power reset switch, one or more patient table positioning motors, one or more patient table rotational motors, and the like. The table actuator interconnect 330 may include one or more physical monitoring contacts coupled to, integrated with, detachably attached to, or the like, the patient table of the proton beam delivery system 140 or 142. As one example, the control contacts 332 of the table actuator interconnect 330 can operatively couple the table actuator interconnect 330 to one or more of a component voltage sensor, a component current sensor, one or more table position sensors, one or more table angle sensors, and the like. The table actuator interconnect 330 may include one or more logical or electronic devices including but not limited to jumper contacts, solder contacts, integrated circuits, logic gates, flip flops, gate arrays, programmable gate arrays, and the like.

The gantry actuator interconnect 340 is operable to operatively couple an electrical, electronic, or like component of at least one gantry actuator of the proton beam delivery system 140 or 142 respectively to the component interface channel 240 or 242. The gantry actuator interconnect 340 may include one or more physical control contacts 342 coupled to, integrated with, detachably attached to, or the like, at least one motorized actuator of the proton beam delivery system 140 or 142. As one example, the control contacts 342 of the gantry actuator interconnect 340 can operatively couple the gantry actuator interconnect 340 to one or more of a power switch, a power reset switch, one or more patient gantry positioning motors, one or more patient gantry rotational motors, and the like. The gantry actuator interconnect 340 may include one or more physical monitoring contacts coupled to, integrated with, detachably attached to, or the like, the patient gantry of the proton beam delivery system 140 or 142. As one example, the control contacts 342 of the gantry actuator interconnect 340 can operatively couple the gantry actuator interconnect 340 to one or more of a component voltage sensor, a component current sensor, one or more gantry position sensors, one or more gantry angle sensors, and the like. The gantry actuator interconnect 340 may include one or more logical or electronic devices including but not limited to jumper contacts, solder contacts, integrated circuits, logic gates, flip flops, gate arrays, programmable gate arrays, and the like.

The chair actuator interconnect 350 is operable to operatively couple an electrical, electronic, or like component of at least one chair actuator of the proton beam delivery system 140 or 142 respectively to the component interface channel 240 or 242. The chair actuator interconnect 350 may include one or more physical control contacts 352 coupled to, integrated with, detachably attached to, or the like, at least one motorized actuator of the proton beam delivery system 140 or 142. As one example, the control contacts 352 of the chair actuator interconnect 350 can operatively couple the chair actuator interconnect 350 to one or more of a power switch, a power reset switch, one or more patient chair positioning motors, one or more patient chair rotational motors, and the like. The chair actuator interconnect 350 may include one or more physical monitoring contacts coupled to, integrated with, detachably attached to, or the like, the patient chair of the proton beam delivery system 140 or 142. As one example, the control contacts 352 of chair actuator interconnect 350 can operatively couple the chair actuator interconnect 350 to one or more of a component voltage sensor, a component current sensor, one or more chair position sensors, one or more chair angle sensors, and the like. The chair actuator interconnect 350 may include one or more logical or electronic devices including but not limited to jumper contacts, solder contacts, integrated circuits, logic gates, flip flops, gate arrays, programmable gate arrays, and the like.

The proton beam positioner interconnect 360 is operable to operatively couple an electrical, electronic, or like component of at least one proton beam actuator of the proton beam delivery system 140 or 142 respectively to the component interface channel 240 or 242. The proton beam positioner interconnect 360 may include one or more physical control contacts 362 coupled to, integrated with, detachably attached to, or the like, at least one motorized actuator of the proton beam delivery system 140 or 142. As one example, the control contacts 362 of the proton beam positioner interconnect 360 can operatively couple the proton beam positioner interconnect 360 to one or more of a power switch, a power reset switch, one or more patient proton beam positioning motors, one or more patient proton beam rotational motors, and the like. The proton beam positioner interconnect 360 may include one or more physical monitoring contacts coupled to, integrated with, detachably attached to, or the like, the patient proton beam of the proton beam delivery system 140 or 142. As one example, the control contacts 362 of the proton beam positioner interconnect 360 can operatively couple the proton beam positioner interconnect 360 to one or more of a component voltage sensor, a component current sensor, one or more proton beam position sensors, one or more proton beam angle sensors, and the like. The proton beam positioner interconnect 360 may include one or more logical or electronic devices including but not limited to jumper contacts, solder contacts, integrated circuits, logic gates, flip flops, gate arrays, programmable gate arrays, and the like.

The proton beam energy interconnect 370 is operable to operatively couple an electrical, electronic, or like component of at least one proton beam actuator of the proton beam delivery system 140 or 142 respectively to the component interface channel 240 or 242. The proton beam energy interconnect 370 may include one or more physical control contacts 372 coupled to, integrated with, detachably attached to, or the like, at least one motorized actuator of the proton beam delivery system 140 or 142. As one example, the control contacts 372 of the proton beam energy interconnect 370 can operatively couple the proton beam energy interconnect 370 to one or more of a power switch, a power reset switch, one or more patient proton beam positioning motors, one or more patient proton beam rotational motors, and the like. The proton beam energy interconnect 370 may include one or more physical monitoring contacts coupled to, integrated with, detachably attached to, or the like, the patient proton beam of the proton beam delivery system 140 or 142. As one example, the control contacts 372 of the proton beam energy interconnect 370 can operatively couple the proton beam energy interconnect 370 to one or more of a component voltage sensor, a component current sensor, one or more proton beam distribution sensors, one or more proton beam density sensors, and the like. The proton beam energy interconnect 370 may include one or more logical or electronic devices including but not limited to jumper contacts, solder contacts, integrated circuits, logic gates, flip flops, gate arrays, programmable gate arrays, and the like.

The patient positioner interconnect 380 is operable to operatively couple an electrical, electronic, or like component of at least one patient positioner of the proton beam delivery system 140 or 142 respectively to the component interface channel 240 or 242. The patient positioner interconnect 380 may include one or more physical control contacts 382 coupled to, integrated with, detachably attached to, or the like, at least one motorized actuator of the proton beam delivery system 140 or 142. As one example, the control contacts 382 of the patient positioner interconnect 380 can operatively couple the patient positioner interconnect 380 to one or more of a power switch, a power reset switch, one or more patient alignment positioning motors, one or more patient alignment rotational motors, and the like. The patient positioner interconnect 380 may include one or more physical monitoring contacts coupled to, integrated with, detachably attached to, or the like, the patient alignment of the proton beam delivery system 140 or 142. As one example, the control contacts 382 of the patient positioner interconnect 380 can operatively couple the patient positioner interconnect 380 to one or more of a component voltage sensor, a component current sensor, one or more patient alignment position sensors, one or more patient alignment angle sensors, and the like. The patient positioner interconnect 380 may include a positioner feedback component operable to modify one or more of position and orientation of one or more of a table, chair, or gantry with respect to a particular portion of a body of a biological organism, patient, and the like. The patient positioner interconnect 380 may include one or more logical or electronic devices including but not limited to jumper contacts, solder contacts, integrated circuits, logic gates, flip flops, gate arrays, programmable gate arrays, and the like.

The imager interconnect 390 is operable to operatively couple an electrical, electronic, or like component of at least one proton beam actuator of the proton beam delivery system 140 or 142 respectively to the component interface channel 240 or 242. The imager interconnect 390 may include one or more physical control contacts 392 coupled to, integrated with, detachably attached to, or the like, at least one motorized actuator of the proton beam delivery system 140 or 142. As one example, the control contacts 392 of the imager interconnect 390 can operatively couple the imager interconnect 390 to one or more of a power switch, a power reset switch, one or more patient proton beam positioning motors, one or more patient proton beam rotational motors, and the like. The imager interconnect 390 may include one or more physical monitoring contacts coupled to, integrated with, detachably attached to, or the like, the patient proton beam of the proton beam delivery system 140 or 142. As one example, the control contacts 392 of the imager interconnect 390 can operatively couple the imager interconnect 390 to one or more of a component voltage sensor, a component current sensor, a brightness sensor, a color sensor, a visual sensor, an infrared sensor, and the like. The imager interconnect 390 may include one or more logical or electronic devices including but not limited to jumper contacts, solder contacts, integrated circuits, logic gates, flip flops, gate arrays, programmable gate arrays, and the like.

Figure 4:
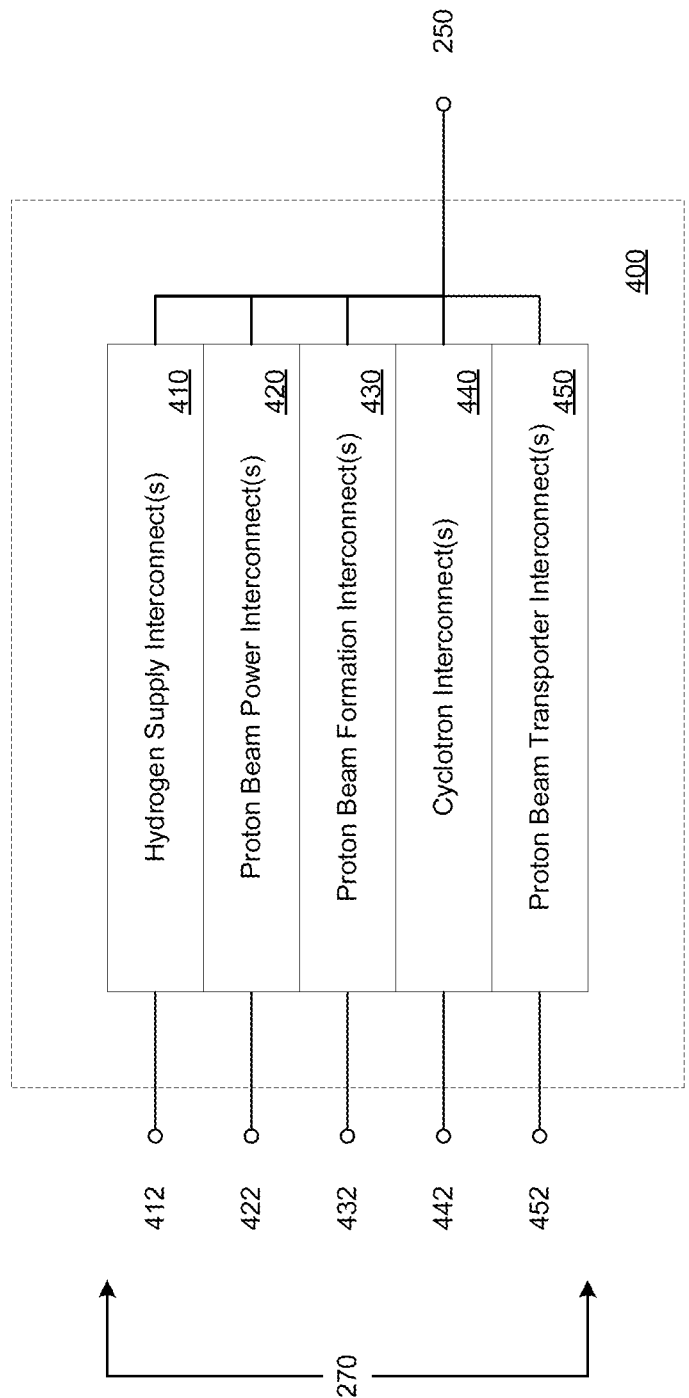
FIG. 4 illustrates a proton beam emitting component interface, further to the proton beam system gateway of FIG. 2, according to an embodiment.

FIG. 4 illustrates an example proton beam emitting component interface, further to the example proton beam system gateway of FIG. 2. As illustrated by way of example in FIG. 4, an example proton beam emitting component interface 400 includes at least one hydrogen supply interconnect 410, at least one proton beam power interconnect 420, at least one proton beam formation interconnect 430, at least one cyclotron interconnect 440, and at least one proton beam transporter interconnect 450.

The hydrogen supply interconnect 410 is operable to operatively couple an electrical, electronic, or like component of at least one hydrogen supply of the proton beam emitting system 130 to the component interface channel 250. The hydrogen supply interconnect 410 may include one or more physical control contacts 412 coupled to, integrated with, detachably attached to, or the like, at least one motorized actuator of the proton beam emitting system 130. As one example, the control contacts 412 of the hydrogen supply interconnect 410 can operatively couple the hydrogen supply interconnect 410 to one or more of a power switch, a power reset switch, a hydrogen gas flow controller, a liquid hydrogen flow controller, an ionic hydrogen generator, and the like. The hydrogen supply interconnect 410 may include one or more physical monitoring contacts coupled to, integrated with, detachably attached to, or the like, the hydrogen supply of the proton beam emitting system 130. As one example, the control contacts 412 of the hydrogen supply interconnect 410 can operatively couple the hydrogen supply interconnect 410 to one or more of a component voltage sensor, a component current sensor, a hydrogen flow rate sensor, a hydrogen charge level sensor, a hydrogen supply temperature sensor, and the like. The hydrogen supply interconnect 410 may include one or more logical or electronic devices including but not limited to jumper contacts, solder contacts, integrated circuits, logic gates, flip flops, gate arrays, programmable gate arrays, and the like.

The proton beam power interconnect 420 is operable to operatively couple an electrical, electronic, or like component of at least one proton beam generator of the proton beam emitting system 130 to the component interface channel 250. The proton beam power interconnect 420 may include one or more physical control contacts 422 coupled to, integrated with, detachably attached to, or the like, at least one motorized actuator of the proton beam emitting system 130. As one example, the control contacts 422 of the proton beam power interconnect 420 can operatively couple the proton beam power interconnect 420 to one or more of a power switch, a power reset switch, a current source controller, a voltage source controller, and the like. The proton beam power interconnect 420 may include one or more physical monitoring contacts coupled to, integrated with, detachably attached to, or the like, the proton beam generator of the proton beam emitting system 130. As one example, the control contacts 422 of the proton beam power interconnect 420 can operatively couple the proton beam power interconnect 420 to one or more of a component voltage sensor, a component current sensor, a proton beam output magnitude sensor, a proton beam generator temperature sensor, and the like. The proton beam power interconnect 420 may include one or more logical or electronic devices including but not limited to jumper contacts, solder contacts, integrated circuits, logic gates, flip flops, gate arrays, programmable gate arrays, and the like.

The proton beam formation interconnect 430 is operable to operatively couple an electrical, electronic, or like component of at least one proton beam generator of the proton beam emitting system 130 to the component interface channel 250. The proton beam formation interconnect 430 may include one or more physical control contacts 432 coupled to, integrated with, detachably attached to, or the like, at least one motorized actuator of the proton beam emitting system 130. As one example, the control contacts 432 of the proton beam formation interconnect 430 can operatively couple the proton beam formation interconnect 430 to one or more of a power switch, a power reset switch, a current source controller, a voltage source controller, and the like. The proton beam formation interconnect 430 may include one or more physical monitoring contacts coupled to, integrated with, detachably attached to, or the like, the proton beam generator of the proton beam emitting system 130. As one example, the control contacts 432 of the proton beam formation interconnect 430 can operatively couple the proton beam formation interconnect 430 to one or more of a component voltage sensor, a component current sensor, a proton beam output magnitude sensor, a proton beam distribution sensor, and the like. The sensors of the proton beam formation interconnect 430 can detect characteristics of a proton beam at or near the point of generation of the proton beam, as opposed to corresponding proton beam delivery sensors that can detect characteristics of the proton beam at or near a point of application. The proton beam formation interconnect 430 may include one or more logical or electronic devices including but not limited to jumper contacts, solder contacts, integrated circuits, logic gates, flip flops, gate arrays, programmable gate arrays, and the like.

The cyclotron interconnect 440 is operable to operatively couple an electrical, electronic, or like component of at least one proton beam generator of the proton beam emitting system 130 to the component interface channel 250. The cyclotron interconnect 440 may include one or more physical control contacts 442 coupled to, integrated with, detachably attached to, or the like, at least one motorized actuator of the proton beam emitting system 130. As one example, the control contacts 442 of the cyclotron interconnect 440 can operatively couple the cyclotron interconnect 440 to one or more of a power switch, a power reset switch, a current source controller, a voltage source controller, and the like. The cyclotron interconnect 440 may include one or more physical monitoring contacts coupled to, integrated with, detachably attached to, or the like, the proton beam generator of the proton beam emitting system 130. As one example, the control contacts 442 of the cyclotron interconnect 440 can operatively couple the cyclotron interconnect 440 to one or more of a component voltage sensor, a component current sensor, a proton generation rate sensor, a hydrogen intake rate sensor, a particle accelerator energy level sensor, and the like. The sensors of the cyclotron interconnect 440 can detect characteristics of a proton beam at or near the point of generation of the proton beam, as opposed to corresponding proton beam delivery sensors that can detect characteristics of the proton beam at or near a point of application. The cyclotron interconnect 440 may include one or more logical or electronic devices including but not limited to jumper contacts, solder contacts, integrated circuits, logic gates, flip flops, gate arrays, programmable gate arrays, and the like.

The proton beam transporter interconnect 450 is operable to operatively couple an electrical, electronic, or like component of at least one proton beam generator of the proton beam emitting system 130 to the component interface channel 250. The proton beam transporter interconnect 450 may include one or more physical control contacts 452 coupled to, integrated with, detachably attached to, or the like, at least one motorized actuator of the proton beam emitting system 130. As one example, the control contacts 452 of the proton beam transporter interconnect 450 can operatively couple the proton beam transporter interconnect 450 to one or more of a power switch, a power reset switch, a current source controller, a voltage source controller, and the like. The proton beam transporter interconnect 450 may include one or more physical monitoring contacts coupled to, integrated with, detachably attached to, or the like, the proton beam generator of the proton beam emitting system 130. As one example, the control contacts 452 of the proton beam transporter interconnect 450 can operatively couple the proton beam transporter interconnect 450 to one or more of a proton beam voltage sensor, a proton beam current sensor, a proton flow rate sensor, a proton beam charge sensor, and the like. The sensors of the proton beam transporter interconnect 450 can detect characteristics of a proton beam at or near one or more points of splitting of the proton beam from a proton beam emitting system 130 to one or more proton beam delivery systems 140 and 142, as opposed to corresponding proton beam delivery sensors that can detect characteristics of the proton beam at or near a point of application. The proton beam transporter interconnect 450 may include one or more logical or electronic devices including but not limited to jumper contacts, solder contacts, integrated circuits, logic gates, flip flops, gate arrays, programmable gate arrays, and the like.

FIG. 5 illustrates an example system memory, further to the example proton beam system gateway of FIG. 2. As illustrated by way of example in FIG. 5, an example system memory 500 includes an operating system 510, a component state engine 520, a component topology engine 530, a control authorization engine 540, a network interface engine 550, and a device command processor 560.

The operating system 510 includes hardware control instructions and program execution instructions. The operating system 510 may be a high level operating system, a server operating system, an embedded operating system, or a boot loader. The operating system 510 may include one or more instructions operable specifically with or only with the system processor 210. The operating system 510 may be operable to control execution of one or more of the component state engine 520, the component topology engine 530, the control authorization engine 540, the network interface engine 550, and the device command processor 560.

The component state engine 520 is operable to identify one or more operating states associated with one or more components of one or more of the proton beam emitting system 130 and the first and second proton beam delivery systems 140 and 142. As one example, operating states can include an operational state and a fault state. An example operational state can indicate that a component is operating normally, is not in need of servicing, or the like. An example fault state can indicate that a component is not operating normally, is in need of servicing, or the like. The component state engine 520 can identify operating states based on input received from one or more of the interconnects of the proton beam delivery component interfaces 300 and 302 and the proton beam emitting component interface 400. The component state engine 520 may include at least one of a component state processor 522 and a component interlock processor 524.

The component state processor 522 is operable to determine at least one operating state of at least one corresponding component based on input from one or more of the interconnects of the proton beam delivery component interfaces 300 and 302 and the proton beam emitting component interface 400. In some implementations, the component state processor 522 includes an operating state translation portion operable to convert an operating state input into an operating state. As one example, the component state processor 522 can associate an operating state input satisfying an operating state threshold with an operational state, and can associate an operating state input not satisfying an operating state threshold with a fault state. As another example, an operating state threshold can be a particular voltage level, current level, hydrogen flow rate, flow rate, charge level, or the like. The component state processor 522 may be operable to obtain one or more operating state thresholds from at least one interlock template associated with a corresponding component. The interlock template can include a structured data file. As one example, the interlock template can be an XML file or the like. The interlock template may correspond to a particular configuration of the proton beam emitting system 130 and the first and second proton beam delivery systems 140 and 142. The interlock template may correspond to a particular configuration associated with a particular model or type of beam emitting system or beam delivery system corresponding respectively to the proton beam emitting system 130 and the first and second proton beam delivery systems 140 and 142.

The component interlock processor 524 is operable to determine at least one operating state of at least one corresponding device including at least one component based on input from one or more of the interconnects of the proton beam delivery component interfaces 300 and 302 and the proton beam emitting component interface 400. The component interlock processor 524 may be operable to obtain one or more device interlock relationships with respect to one or more components from the interlock template associated with the corresponding component and device. The interlock template may include a dependency relationship between one or more components and one or more devices including the components. As one example, the interlock template can define an interlock sensor device including multiple sensor components, each configured to detect a different characteristic. As another example, an interlock can correspond to a collection of components, and can correspond to a device including those components. Thus, an interlock can be interchangeable with a device with respect to a control and monitoring context.

The component topology engine 530 is operable to generate a representation of at least a portion of the proton beam emitting system 130 and the first and second proton beam delivery systems 140 and 142 in accordance with multiple representation structures. The component topology engine 530 may obtain a representation structure based on input received from an interlock template associated with the proton beam emitting system 130 and the first and second proton beam delivery systems 140 and 142. As one example, the component topology engine 530 can generate a hierarchical topology corresponding to an interlock including components, a greater interlock including an interlock, a greater interlock including an interlock and a component, any combination thereof, or the like. As another example, the component topology engine 530 can generate a schematic topology corresponding to one or more operatively coupling between components, interlock, or any combination thereof, within at least a portion of at least one of the proton beam emitting system 130 and the first and second proton beam delivery systems 140 and 142. The component topology engine 530 may include at least one of a hierarchy processing engine 532 and a schematic processing engine 534.

The hierarchy processing engine 532 is operable to generate a representation of at least a portion of the proton beam emitting system 130 and the first and second proton beam delivery systems 140 and 142 in accordance with a hierarchical representation structure. As one example, a hierarchical presentation structure can include a nested list of components and interlocks. As another example, a hierarchical structure can include one or more components nested under respective interlocks, and can further include interlocks further nested under additional interlocks in a multilevel hierarchical structure. A hierarchical structure can include a portion of a hierarchy corresponding to at least one of the proton beam emitting system 130 and the first and second proton beam delivery systems 140 and 142. As one example, a portion of a hierarchy can include a subset of interlocks and the components or interlocks contained thereby. Thus, hierarchy processing engine 532 may generate a portion of a hierarchical structure corresponding to a collection of at least one interlock or component associated with a containing or like relationship therebetween. As one example, a containing relationship can be a relationship where a component is integrated into an interlock or device corresponding to an interlock.

The schematic processing engine 534 is operable to generate a representation of at least a portion of the proton beam emitting system 130 and the first and second proton beam delivery systems 140 and 142 in accordance with a schematic representation structure. As one example, a schematic presentation structure can include a blueprint structure, an engineering structure, an electrical structure, a block structure, or the like including one or more components and interlocks. As another example, a schematic structure can include one or more components and interlocks operatively coupled in an arrangement corresponding to a physical structure of the components and interlocks. A schematic structure can include a portion of a schematic corresponding to at least one of the proton beam emitting system 130 and the first and second proton beam delivery systems 140 and 142. As one example, a portion of a schematic can include a subset of interlocks and the components or interlocks connected thereto, directly or indirectly. Thus, schematic processing engine 534 may generate a portion of a schematic structure corresponding to a collection of at least one interlock or component associated with a coupling, connecting, or like relationship therebetween. As one example, a connecting relationship can be a relationship where a component is electrically connected or physically attached to an interlock or device corresponding to an interlock.

The control authorization engine 540 is operable to authorize execution of one or more control instructions to modify one or more operating states of one or more components of one or more of the proton beam emitting system 130 and the first and second proton beam delivery systems 140 and 142. The control authorization engine 540 may be operable to accept one or more control authorization indications during a predetermined control authorization instruction acceptance period. The acceptance period may correspond to a period in seconds, minutes during which a control authorization instruction may be validly received. When a control authorization instruction is validly received, the control authorization engine 540 can allow execution of control instructions. As one example, the control authorization engine 540 can allow execution of control instructions by allowing transmission of a control instruction from the device command processor 564 to the network interface engine 550. When a control authorization instruction is not validly received, the control authorization engine 540 can block execution of control instructions. As one example, the control authorization engine 540 can block execution of control instructions by blocking transmission of a control instruction from the device command processor 564 to the network interface engine 550. The control authorization engine 540 may include an authorization input engine 542.

The authorization input engine 542 is operable to receive input from the control authorization toggle switch 150 and to receive, generate, obtain, or the like, a control authorization instruction in response to the input from the control authorization toggle switch 150. The authorization input engine 542 may receive one or more of an analog signal, a digital signal, a binary signal, or any combination thereof, from the control authorization toggle switch 150.

The network interface engine 550 is operable to communicate one or more control instructions, operating states, control information, monitoring information, any combination thereof, or the like, to any of the component interfaces 300, 302 and 400, and communication interfaces 220 and 230. The network interface engine 550 may include at least one of an interconnect interface controller 552, a control interface controller 554, and a monitor interface controller 556.

The interconnect interface controller 552 is operable to communicate one or more control instructions, operating states, control information, monitoring information, any combination thereof, or the like, to any of the component interfaces 300, 302 and 400. The interconnect interface controller 552 may be operable to transmit analog signals, digital signals, any combination thereof, or the like, to any interconnect operatively coupled to any of the component interfaces 300, 302 and 400. The interconnect interface controller 552 can transmit instructions in accordance and compatible with any analog or digital channel, wire, trace, or the like operatively coupled to any of the component interfaces 300, 302 and 400.

The control interface controller 554 is operable to communicate one or more control instructions, control information, any combination thereof, or the like, by the system control communication interface 220. The control interface controller 554 may be operable to transmit and receive a secure, dedicated, tunneled, packetized, encrypted, tokenized, or like communication by the system control communication interface 220. The control interface controller 554 can transmit instructions in accordance and compatible with any network channel, wireless channel, telecommunication channel, or the like operatively coupled to the system control communication interface 220.

The monitor interface controller 556 is operable to communicate one or more monitoring instructions, operating states, monitoring information, any combination thereof, or the like, by the system monitor communication interface 230. The monitor interface controller 556 may be operable to transmit and receive a secure, dedicated, tunneled, packetized, encrypted, tokenized, or like communication by the system monitor communication interface 230. The monitor interface controller 556 can transmit instructions in accordance and compatible with any network channel, wireless channel, telecommunication channel, or the like operatively coupled to system control communication interface 220. The control interface controller 554 and the monitor interface controller 556 can advantageously be decoupled, isolated, or the like, from each other to ensure independent and secure communication for both secure control of proton beam hardware and reliable monitoring of proton beam hardware.

The device command processor 560 is operable to generate a device command executable by or at any of the interconnects 310, 320, 330, 340, 350, 360, 370, 380, 390, 410, 420, 430, 440 and 450. The device command processor 560 may include an interconnect command translator 562. The interconnect command translator 562 is operable to generate at least one device command compatible with at least one of the interconnects 310, 320, 330, 340, 350, 360, 370, 380, 390, 410, 420, 430, 440 and 450 to modify an operating state of at least one component coupled thereto.

Figure 6:
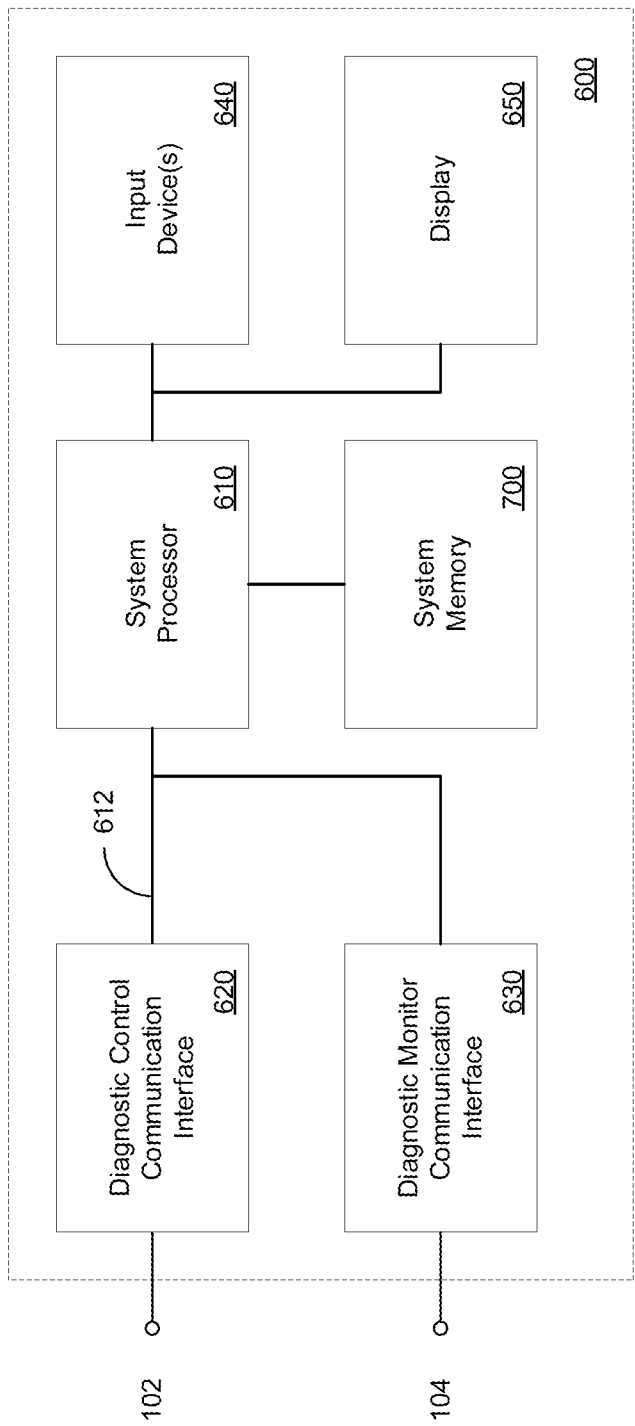
FIG. 6 illustrates a diagnostic system, further to the system of FIG. 1, according to an embodiment.

FIG. 6 illustrates an example diagnostic system, further to the example system of FIG. 1. As illustrated by way of example in FIG. 6, an example diagnostic system 600 includes a system processor 610, a system memory 700, a diagnostic control communication interface 620, a diagnostic monitor communication interface 630, one or more input devices 640, and a display 650.

The system processor 610 is operable to execute one or more instructions associated with input from the diagnostic control communication interface 620, the diagnostic monitor communication interface 630, the input devices 640, and the display 650. The system processor 610 can correspond in one or more of structure and operation to the system processor 210. The system memory 700 is operable to store data associated with the diagnostic system 600. The system memory 700 can correspond in one or more of structure and operation to the system memory 500.

The diagnostic control communication interface 620 is operable to receive and transmit one or more instructions by the service control channel 102 to the proton beam system gateway 200. The diagnostic control communication interface 620 may include a command translation unit operable to convert one or more instructions between a processor format compatible with the system processor 610 and a communication format compatible with one or more of the service control channel 102 and the proton beam system gateway 200. The diagnostic control communication interface 620 may include one or more logical or electronic devices including but not limited to integrated circuits, logic gates, flip flops, gate arrays, programmable gate arrays, and the like. Any electrical, electronic, or like devices, or components associated with the diagnostic control communication interface 620 can also be associated with, integrated with, integrable with, replaced by, supplemented by, complemented by, or the like, the system processor 610 or any component thereof.

The diagnostic monitor communication interface 630 is operable to receive and transmit one or more instructions by the service monitor channel 104 to the proton beam system gateway 200. The diagnostic monitor communication interface 630 may include a command translation unit operable to convert one or more instructions between a processor format compatible with the system processor 610 and a communication format compatible with one or more of the service monitor channel 104 and the proton beam system gateway 200. The diagnostic monitor communication interface 630 may include one or more logical or electronic devices including but not limited to integrated circuits, logic gates, flip flops, gate arrays, programmable gate arrays, and the like. Any electrical, electronic, or like devices, or components associated with the diagnostic monitor communication interface 630 can also be associated with, integrated with, integrable with, replaced by, supplemented by, complemented by, or the like, the system processor 610 or any component thereof.

The input devices 640 are operable to receive control instructions and monitoring instructions. The input devices may receive instructions from a user by one or more human-computer interface devices. As one example, human-computer interface devices can include one or more notebook computers, desktop computers, tablets, smartphones, printers, scanners, telephony endpoints, videoconferencing endpoints, keyboards, mice, trackpads, gaming peripherals, monitors, televisions, and the like. The display 650 is operable to display one or more graphical user interfaces for remote control and remote monitoring. In some implementations, the display 650 includes an electronic display. The electronic display may include a liquid crystal display (LCD), a light-emitting diode (LED) display, an organic light-emitting diode (OLED) display, or the like.

FIG. 7 illustrates an example system memory further to the example diagnostic system of FIG. 6. As illustrated by way of example in FIG. 7, an example system memory 700 includes an operating system 710, an interface input engine 720, a network interface engine 730, and a presentation engine 740.

The operating system 710 includes hardware control instructions and program execution instructions. The operating system 710 may be a high level operating system, a server operating system, a desktop operating system, an embedded operating system, or a boot loader The operating system 710 may include one or more instructions operable specifically with or only with the system processor 610. The operating system 710 may be operable to control execution of one or more of the interface input engine 720, the network interface engine 730, and the presentation engine 740. The interface input engine 720 is operable to obtain one or more inputs from one or more of the input devices 640. As one example, the interface input engine 720 includes one or more instructions for obtaining, parsing, combining, translating, or any combination thereof, or the like, input from at least one of the input devices 640.

The network interface engine 730 is operable to communicate one or more control instructions, operating states, control information, monitoring information, any combination thereof, or the like, to any of the communication interfaces 620 and 630. The network interface engine 730 may include a control interface controller 732 and a monitor interface controller 734. The control interface controller 732 is operable to communicate one or more control instructions, control information, any combination thereof, or the like, by the diagnostic control communication interface 620. The control interface controller 732 may be operable to transmit and receive a secure, dedicated, tunneled, packetized, encrypted, tokenized, or like communication by the diagnostic control communication interface 620. The control interface controller 732 can transmit instructions in accordance and compatible with any network channel, wireless channel, telecommunication channel, or the like operatively coupled to the diagnostic control communication interface 620.

The monitor interface controller 734 is operable to communicate one or more monitoring instructions, operating states, monitoring information, any combination thereof, or the like, by the diagnostic monitor communication interface 630. The monitor interface controller 734 may be operable to transmit and receive a secure, dedicated, tunneled, packetized, encrypted, tokenized, or like communication by the diagnostic monitor communication interface 630. The monitor interface controller 734 can transmit instructions in accordance and compatible with any network channel, wireless channel, telecommunication channel, or the like operatively coupled to diagnostic monitor communication interface 630. The control interface controller 732 and the monitor interface controller 734 can advantageously be decoupled, isolated, or the like, from each other to ensure independent and secure communication for both secure control of proton beam hardware and reliable monitoring of proton beam hardware.

The presentation engine 740 is operable to generate one or more graphical user interfaces, presentations, control affordances, operating state indications, hierarchies, schematics, and the like associated with one or more of the proton beam emitting system 130, the proton beam delivery systems 140 and 142, the proton beam system gateway 200, the control authorization toggle switch 160, and the diagnostic system 600. The presentation engine 740 may be operable to modify any presentation in response to any user input, control instruction, monitoring instruction, or the like, received thereby. The presentation engine 740 may include at least one of a hierarchy presentation engine 742, a schematic presentation engine 744, an interlock presentation engine 746, and a user presentation controller 748.

The hierarchy presentation engine 742 is operable to generate at least one hierarchical presentation having a hierarchical structure corresponding to at least a portion of one or more of the proton beam emitting system 130, the proton beam delivery systems 140 and 142, the proton beam system gateway 200, and the control authorization toggle switch 160. The hierarchy presentation engine 742 may be operable to generate a hierarchical presentation based on a hierarchy generated by or at the component topology engine 530 or the hierarchy processing engine 532. The hierarchy presentation engine 742 may be operable to traverse at least a portion of a hierarchy generated by or at the component topology engine 530 or the hierarchy processing engine 532, to generate the hierarchical presentation. As one example, the hierarchy presentation engine 742 can generate a hierarchy having a nested list structure, including an operating state indicator associated with one or more items in the nested list. As another example, the operating state indicator can include an icon, glyph, coloration, image, character, or any combination thereof, or the like.

The schematic presentation engine 744 is operable to generate at least one schematic presentation having a schematic structure corresponding to at least a portion of one or more of the proton beam emitting system 130, the proton beam delivery systems 140 and 142, the proton beam system gateway 200, and the control authorization toggle switch 160. The schematic presentation engine 744 may be operable to generate a schematic presentation based on a schematic generated by or at the component topology engine 530 or the schematic processing engine 534. The schematic presentation engine 744 may be operable to traverse at least a portion of a schematic generated by or at the component topology engine 530 or the schematic processing engine 534, to generate the schematic presentation. As one example, the schematic presentation engine 744 can generate a schematic having a blueprint structure, including an operating state indicator associated with one or more items in the blueprint. As another example, the operating state indicator can include an icon, glyph, coloration, image, character, or any combination thereof, or the like.

The interlock presentation engine 746 is operable to generate one or more operating indicator presentations in accordance with one or more interlock dependency conditions. An interlock dependency condition may correspond to an absolute component dependency, where an interlock is associated with a fault state if a particular component thereof is associated with the fault state. An interlock dependency condition may correspond to an independent component dependency, where an interlock is not associated with a fault state even if a particular component thereof is associated with the fault state. The interlock presentation engine 746 may generate the operating indicator presentations in accordance with at least one of the component state engine 520 and the component interlock processor 524.

The user presentation controller 748 is operable to generate one or more user interfaces based on a user type associated with the user interface. As one example, the user presentation controller 748 can generate a user interface with a clinician view if a user type linked to the user presentation controller 748 corresponds to a clinician. The clinician view may include a simplified user interface associated with one or more of the hierarchical presentation and the schematic presentation, in which component-level presentation are omitted. As another example, the user presentation controller 748 can generate a user interface with a technician view if a user type linked to the user presentation controller 748 corresponds to a technician. The technician view may include a detailed user interface associated with one or more of the hierarchical presentation and the schematic presentation, in which component-level presentation are included. The clinician view may be included within the technician view as a portion thereof.

FIG. 8 illustrates a first example graphical user interface for remote monitoring of a proton beam emitting and delivery system, in accordance with present implementations. As illustrated by way of example in FIG. 8, an example graphical user interface 800 includes a delivery system report interface 810, a system overview report interface 820, an imager report interface 830, a scanning or eye nozzle report interface 840, a gantry actuator report interface 850, and a table or chair actuator report interface 860.

The delivery system report interface 810 includes a portion of the graphical user interface 800 presenting one or more characteristics of a proton beam delivery system among the first and second proton beam delivery systems 140 and 142. As one example, the delivery system report interface 810 can present one or more of a software version number, identifier, or the like executing at the proton beam delivery system 140 or 142, a delivery facility state indicating whether the proton beam delivery systems 140 or 142 is operational, a robot state indicating whether a robotic system associated with the proton beam delivery system 140 or 142 is operational, and a system temperature associated with the proton beam delivery systems 140 or 142. A robot state can include individually or collectively one or more actuators, motors, positions, and the like associated with the proton beam delivery system 140 or 142. The delivery system report interface 810 can advantageously present an intuitive and near-real-time system-level presentation directly obtained from interconnects for one or more interconnects to the proton beam delivery system 140 or 142.

The system overview report interface 820 includes a portion of the graphical user interface 800 presenting one or more interlock states associated with the proton beam delivery system 140 or 142. The system overview report interface 820 may present a flat or non-hierarchical list view of one or more interlocks associated with the proton beam delivery system 104 or 142. The system overview report interface 820 can also include one or more operating state indicators corresponding to one or more of the interlocks presented at the system overview report interface 820. The system overview report interface 820 can advantageously present an intuitive and near-real-time interlock-level presentation directly obtained from interconnects for one or more interconnects to the proton beam delivery system 140 or 142.

The imager report interface 830 includes a portion of the graphical user interface 800 presenting one or more characteristics of a proton beam delivery imager device among the first and second proton beam delivery systems 140 and 142. As one example, the imager report interface 830 can present one or more of an orientation state of a proton beam delivery imager device and one or more interlocks and their corresponding operating state indicators. As one example, an orientation state of the proton beam delivery imager device can include a first position configuration state indicating one or more lateral or angular positions corresponding to the first position configuration state, and a second position configuration state indicating one or more lateral or angular positions corresponding to the second position configuration state. The imager report interface 830 can advantageously present an intuitive and near-real-time interlock-level presentation directly obtained from interconnects for one or more interconnects to the proton beam delivery system 140 or 142.

The scanning or eye nozzle report interface 840 includes a portion of the graphical user interface 800 presenting one or more characteristics of a proton beam scanning nozzle device or a proton beam eye nozzle device among the first and second proton beam delivery systems 140 and 142. As one example, the scanning or eye nozzle report interface 840 can present one or more of an orientation state of a proton beam scanning nozzle device or a proton beam eye nozzle device and one or more interlocks and their corresponding operating state indicators. As one example, an orientation state of the proton beam scanning nozzle device or the proton beam eye nozzle device can include one or more lateral or angular positions corresponding thereto. The scanning or eye nozzle report interface 840 can advantageously present an intuitive and near-real-time interlock-level presentation directly obtained from interconnects for one or more interconnects to the proton beam delivery system 140 or 142. The scanning or eye nozzle report interface 840 may include a scanning or eye nozzle aperture interface 842.

The scanning or eye nozzle aperture interface 842 may include a portion of the graphical user interface 800 presenting one or more proton beam distribution indications, calibration indications, or the like of a proton beam scanning nozzle device or a proton beam eye nozzle device among the first and second proton beam delivery systems 140 and 142. As one example, the scanning or eye nozzle report interface 840 can present one or more distribution indications located at actual locations of distribution of proton beam energy as operating state indicators with respect to a frame. As another example, the scanning or eye nozzle report interface 840 can present one or more calibration indications located at theoretical or ideal locations of distribution of proton beam energy as operating state indicators with respect to a frame. The frame may correspond to a cross-section of a proton beam at a point of receipt at the first or second proton beam delivery system 140 or 142, or point of application corresponding to a patient or the like. As one example, an orientation state of the proton beam scanning nozzle device or the proton beam eye nozzle device can include one or more lateral or angular positions corresponding thereto.

The gantry actuator report interface 850 includes a portion of the graphical user interface 800 presenting one or more characteristics of one or more gantry motors and sensors among the first and second proton beam delivery systems 140 and 142. As one example, the gantry actuator report interface 850 can present one or more of an orientation state of a gantry and one or more interlocks and their corresponding operating state indicators. The table or chair actuator report interface 860 includes a portion of the graphical user interface 800 presenting one or more characteristics of one or more table or chair motors and sensors among the first and second proton beam delivery systems 140 and 142. As one example, the table or chair actuator report interface 860 can present one or more of an orientation state of a table or chair and one or more interlocks and their corresponding operating state indicators. The gantry actuator report interface 850 and the table or chair actuator report interface 860 can advantageously present an intuitive and near-real-time interlock-level presentation directly obtained from interconnects for one or more interconnects to the proton beam delivery system 140 or 142.

Figure 9:
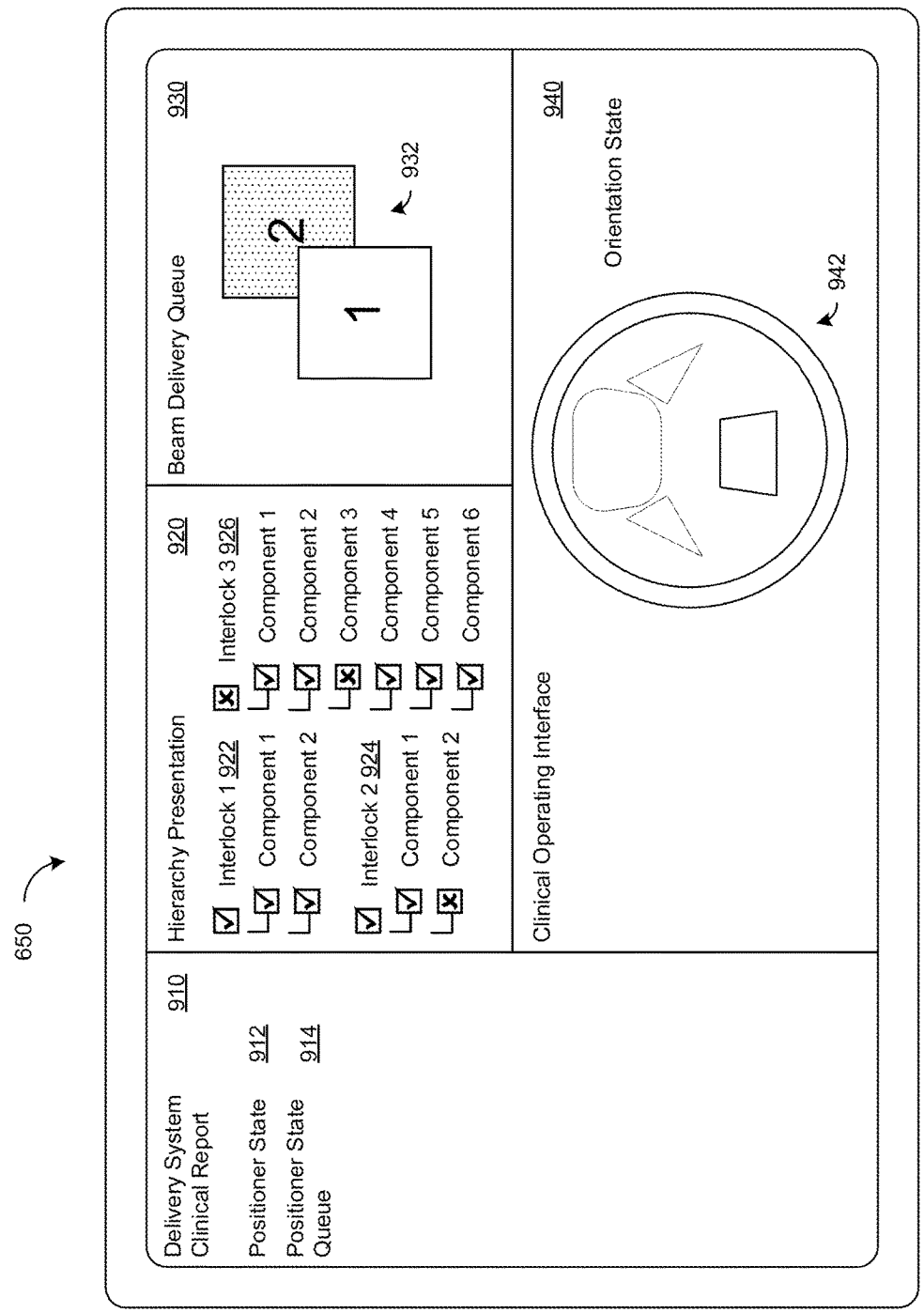
FIG. 9 illustrates a graphical user interface for remote monitoring of a proton beam emitting and delivery system including a hierarchical presentation, according to an embodiment.

FIG. 9 illustrates a second example graphical user interface for remote monitoring of a proton beam emitting and delivery system including a hierarchical presentation, in accordance with present implementations. As illustrated by way of example in FIG. 9, an example graphical user interface 900 includes a delivery system clinical report interface 910, a hierarchy presentation interface 920, a beam delivery queue interface 930, and a clinical operating interface 940.

The delivery system clinical report interface 910 includes a portion of the graphical user interface 900 presenting one or more orientations of one or more motors and sensors among the first and second proton beam delivery systems 140 and 142. The delivery system clinical report interface 910 can advantageously present clinician-centric operating states associated with the first or second proton beam delivery systems 140 or 142 to improve ability to remotely monitor and remotely control the first or second proton beam delivery system 140 or 142 by the diagnostic system 600. The delivery system clinical report interface 910 may include at least one of a positioner state interface 912 and a positioner state queue interface 914. The positioner state interface 912 may present a current state of one or more of a scanning nozzle, eye nozzle, gantry, table, and chair in connection with a clinical operation, treatment, or the like. The positioner state queue interface 914 may present at least one past or future state of one or more of a scanning nozzle, eye nozzle, gantry, table, and chair in connection with a clinical operation, treatment, or the like. As one example, the positioner state queue interface 914 can present at least one past or future state as a list, queue, or the like ordered by time with respect to a relative current time or an absolute start or end time of a clinical operation, treatment, or the like.

The hierarchy presentation interface 920 includes a portion of the graphical user interface 900 presenting one or more interlocks and their corresponding included components for at least a portion of the first or second proton beam delivery systems 140 or 142. The hierarchy presentation interface 920 can advantageously present an intuitive and near-real-time interface including operating states and cascading failure information associated with the first or second proton beam delivery systems 140 or 142 to improve ability to remotely monitor and remotely control the first or second proton beam delivery systems 140 or 142 by the diagnostic system 600. In some implementations, the hierarchy presentation interface 920 includes at least one of first, second, and third interlock hierarchy presentations 922, 924 and 926. The first interlock hierarchy presentation 922 includes a first example hierarchical presentation free of any fault states. In the first example hierarchical presentation, operating states of all components and an interlock including the components are in an operational state.

The second interlock hierarchy presentation 924 includes a second example hierarchical presentation including a component fault state independent of a fault state of an interlock including the fault state component. In the second example hierarchical presentation, an operating state of one component is in a fault state, and an operating state of an interlock including the component is in an operational state. Thus, in this example, failure of a component does not cascade to failure of the interlock. A non-cascading fault state can intuitively indicate a fault state that needs remote control or monitoring at a lower level of urgency.

The third interlock hierarchy presentation 926 includes a third example hierarchical presentation including a component fault state dependent on a fault state of an interlock including the fault state component. In the third example hierarchical presentation, an operating state of one component is in a fault state, and an operating state of an interlock including the component is in a corresponding fault state in response to the fault state of the fault state component. Thus, in this example, failure of a component does cascade to failure of the interlock. A cascading fault state can intuitively indicate a fault state that needs remote control or monitoring at a higher level of urgency.

The beam delivery queue interface 930 includes a portion of the graphical user interface 900 presenting an order of activation of the first and second proton beam delivery systems 140 and 142. The beam delivery queue interface 930 can advantageously present a clinician-centric view of real-time activity of the first or second proton beam delivery system 140 or 142 to improve ability to remotely monitor and remotely control the first or second proton beam delivery system 140 or 142 by the diagnostic system 600. The beam delivery queue interface 930 may include a beam delivery queue stack 932. The beam delivery queue stack 932 includes a portion of the graphical user interface 900 presenting an order of activation of the first and second proton beam delivery systems 140 and 142. The beam delivery queue stack 932 can include more or fewer stacked elements based on the number of proton beam delivery systems operatively coupled to the graphical user interface 900.

The clinical operating interface 940 includes a portion of the graphical user interface 900 presenting one or more orientations of one or more proton beam therapy devices among the first and second proton beam delivery systems 140 and 142. The beam delivery queue interface 930 can advantageously present a clinician-centric view of real-time activity of the first or second proton beam delivery system 140 or 142 to improve ability to remotely monitor and remotely control the first or second proton beam delivery system 140 or 142 by the diagnostic system 600. The clinical operating interface 940 may include a proton beam delivery system state presentation 942. The proton beam delivery system state presentation 942 includes a portion of the graphical user interface 900 presenting a visual representation of at least one of the first and second proton beam delivery systems 140 and 142.

Figure 10:
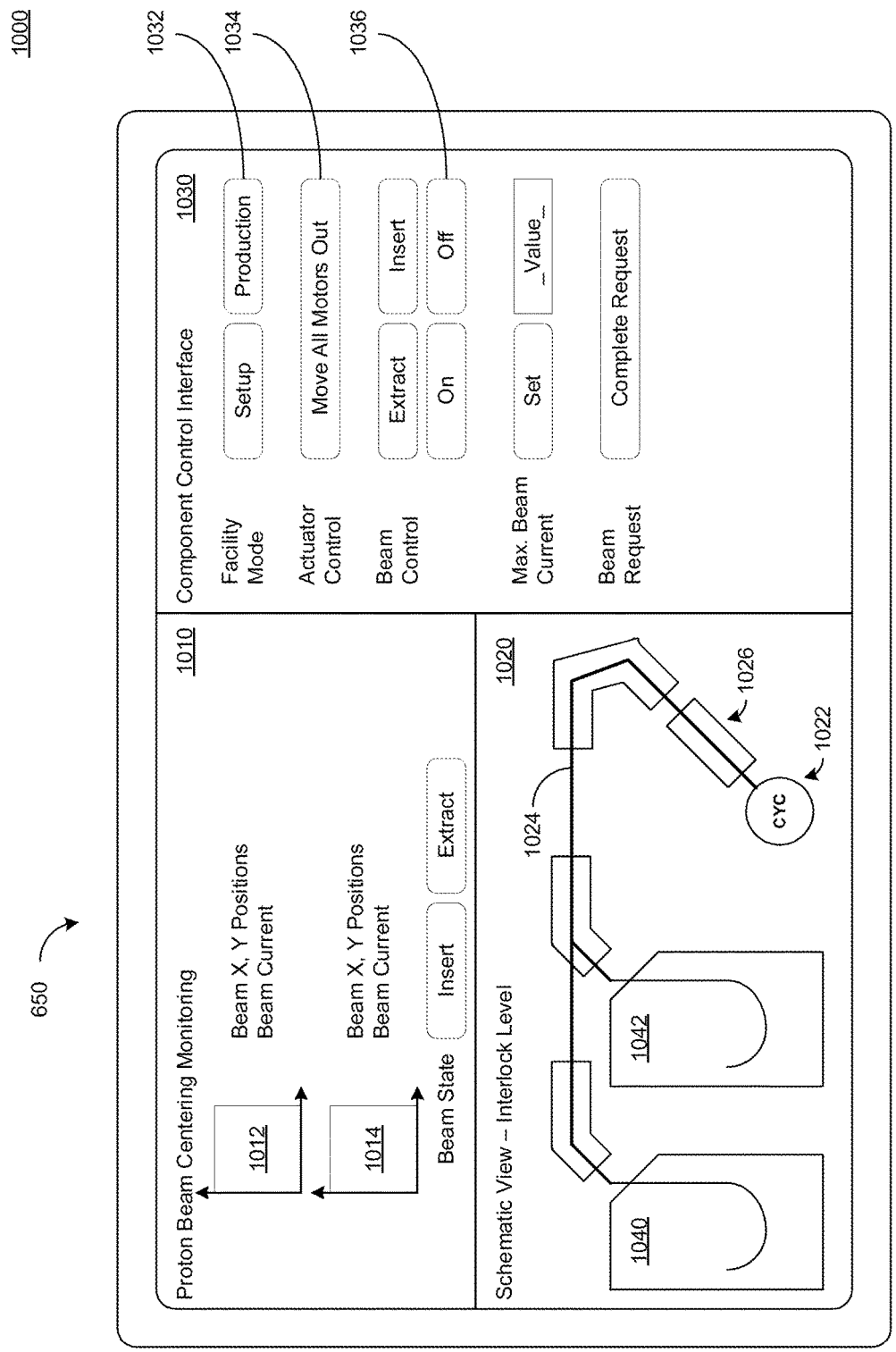
FIG. 10 illustrates a graphical user interface for remote control and remote monitoring of a proton beam emitting and delivery system including an interlock schematic presentation, according to an embodiment.

FIG. 10 illustrates a third example graphical user interface for remote control and remote monitoring of a proton beam emitting and delivery system including an interlock schematic presentation, in accordance with present implementations. As illustrated by way of example in FIG. 10, an example graphical user interface 1000 includes a proton beam centering monitoring interface 1010, an interlock-level schematic view presentation 1020, and a component control interface 1030.

The proton beam centering monitoring interface 1010 includes a portion of the graphical user interface 1000 presenting one or more characteristics of a proton beam scanning nozzle device or a proton beam eye nozzle device among the first and second proton beam delivery systems 140 and 142. As one example, the scanning or eye nozzle report interface 840 can present one or more physical positions with respect to a beam application target area of a proton beam scanning nozzle device or a proton beam eye nozzle device and one or more interlocks and their corresponding operating state indicators, and one or more electrical characteristics of a proton beam with respect to portions of the beam application target area. As one example, the proton beam centering monitoring interface 1010 can present a bell curve or the like indicating a position of highest beam application energy with respect to a center line or the like of the beam application target area. The proton beam centering monitoring interface 1010 can advantageously present an intuitive and near-real-time beam shape presentation directly obtained from interconnects for one or more interconnects to the proton beam delivery system 140 or 142. The proton beam centering monitoring interface 1010 may include at least one of first and second beam output presentations 1012 and 1014. The first and second beam output presentations 1012 and 1014 can correspond to outputs associated respectively with the beam delivery schematic interlocks 1040 and 1042 respectively of the proton beam delivery component interfaces 300 and 302.

The interlock-level schematic view presentation 1020 includes a portion of the graphical user interface 1000 presenting a schematic structure of one or more of the proton beam emitting system 130. The interlock-level schematic view presentation 1020 can include an arbitrary number of beam delivery schematic interlocks 1040 corresponding to the number of proton beam delivery systems operatively coupled to the graphical user interface 1000. The interlock-level schematic view presentation 1020 may include at least one of a cyclotron schematic interlock 1022, at least one schematic proton beam path 1024, one or more beam transport schematic interlocks 1026, and one or more beam delivery schematic interlocks 1040 and 1042.

The cyclotron schematic interlock 1022 includes a portion of the graphical user interface 1000 presenting a schematic structure of the proton beam emitting system 130. The interlock-level schematic view presentation 1020 may present the cyclotron schematic interlock 1022 in relation to the schematic proton beam path 1024 as it travels from its point of generation at the cyclotron of the proton beam emitting system 130 through the beam transport system to one or more of the proton beam delivery systems 140 and 142. The schematic proton beam path 1024 includes a portion of the graphical user interface 1000 presenting a schematic structure of the proton beam throughout the clinical site. The proton beam presented as the schematic proton beam path 1024 may travel by a beam transport path distinct from the channels 150 and 152. The beam transport schematic interlocks 1026 include a portion of the graphical user interface 1000 presenting a schematic structure of one or more devices of a beam transport system for transmitting a proton beam generated at a proton beam emitting system 130 to one or more of the proton beam delivery systems 140 and 142. The beam delivery schematic interlocks 1040 and 1042 include a portion of the graphical user interface 1000 presenting a schematic structure of the proton beam delivery systems 140 and 142. The beam delivery schematic interlocks 1040 and 1042 can correspond to the proton beam delivery systems 140 and 142. The beam delivery schematic interlocks 1040 and 1042 can advantageously indicate proton beam presence and characteristics at the component and interlock levels.

The component control interface 1030 includes a portion of the graphical user interface 1000 presenting one or more control affordances for modifying operating states of one or systems, interlocks, or components of one or more of the proton beam emitting system 130, the first proton beam delivery system 140, and the second proton beam delivery system 142. The component control interface 1030 may include at least one of a facility control interface 1032, an actuator control interface 1034, a beam control interface 1036, and a beam current interface 1038.

The facility control interface 1032 includes a portion of the graphical user interface 1000 presenting one or more control affordances for modifying operating states of the proton beam emitting system 130, the first proton beam delivery system 140, and the second proton beam delivery system 142. The facility control interface 1032 can provide a control authorization instruction to the diagnostic system 600, bypass a control authorization instruction from the control authorization toggle switch 150 in response to an activation of the setup control affordance, or can require a control authorization instruction from the control authorization toggle switch 150 in response to an activation of the setup control affordance.

The actuator control interface 1034 includes a portion of the graphical user interface 1000 presenting one or more control affordances for modifying operating states of one or more of a gantry, chair, table, scanning nozzle, or eye nozzle of one or more of the proton beam delivery systems 140 and 142. The beam control interface 1036 includes a portion of the graphical user interface 1000 presenting one or more control affordances for modifying operating states of one or more proton beams generated by the proton beam emitting system 130. As one example, the beam control interface 1036 can effect one or more of an extract operation, an insert operation an on operation, an off operation, and a beam current magnitude set operation.

Figure 11:
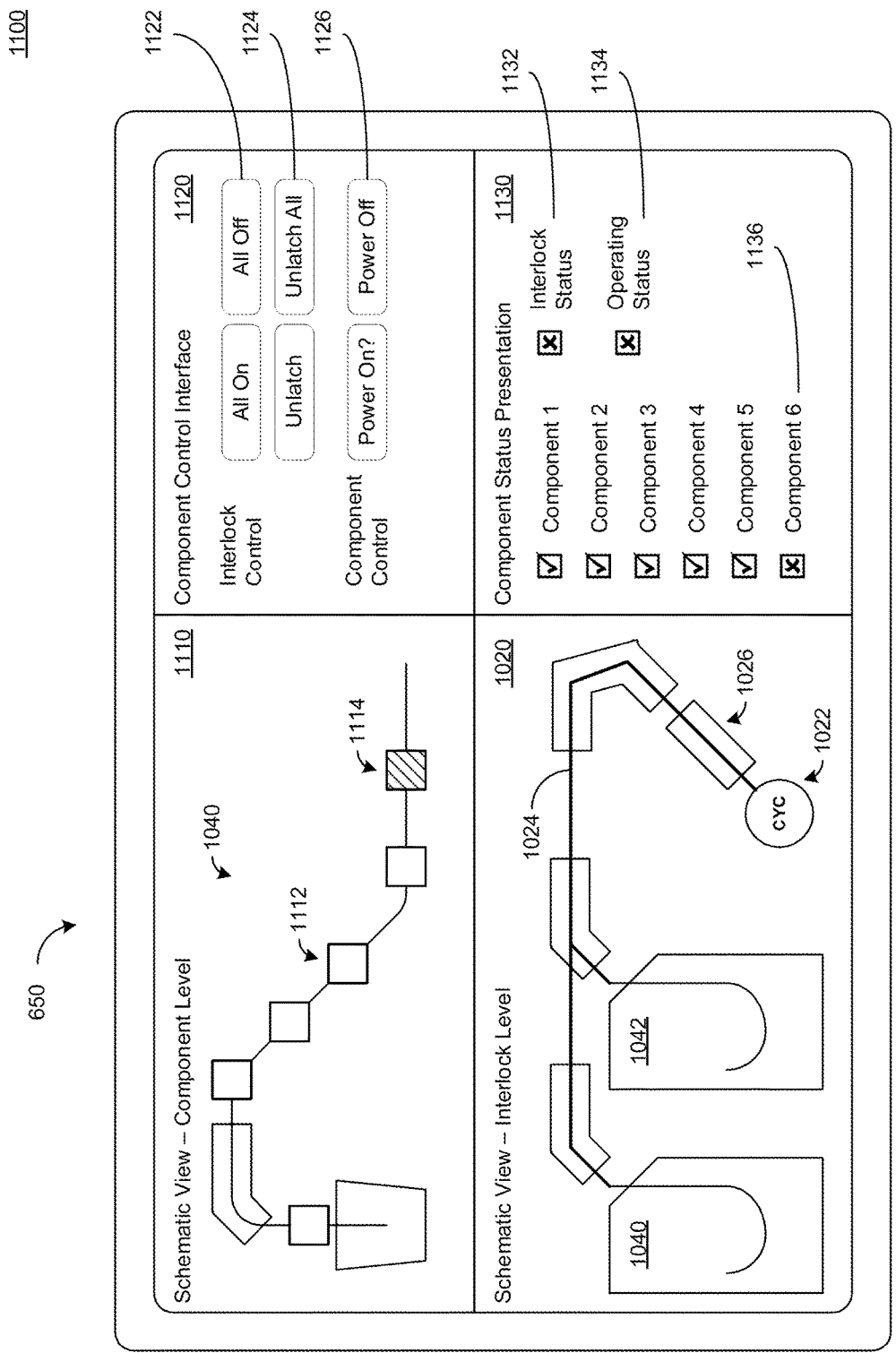
FIG. 11 illustrates a graphical user interface for remote control and remote monitoring of a proton beam emitting and delivery system including an interlock schematic presentation and a component schematic presentation, according to an embodiment.

FIG. 11 illustrates a fourth example graphical user interface for remote control and remote monitoring of a proton beam emitting and delivery system including an interlock schematic presentation and a component schematic presentation, in accordance with present implementations. As illustrated by way of example in FIG. 11, an example graphical user interface includes the interlock-level schematic view presentation 1020, a component-level schematic view presentation 1110, a component control interface 1120, and a component status presentation 1130.

The component-level schematic view presentation 1110 includes a portion of the graphical user interface 1000 presenting a schematic structure including one or more components of one or more of the proton beam emitting system 130, the first proton beam delivery system 140, and the second proton beam delivery system 142. As one example, the component-level schematic view presentation 1110 can present at least one interlock, and its included components, for the beam delivery schematic interlock 1040. The component-level schematic view presentation 1110 can present any schematic structure corresponding to any portion or entirety of any collection of interlocks or components associated with one or more of the proton beam emitting system 130, the proton beam delivery system 140, and the proton beam delivery system 142. The component-level schematic view presentation 1110 may include at least one operational state component presentation 1112 and at least one fault state component presentation 1114.

The operational state component presentation 1112 includes a portion of the graphical user interface 1000 presenting a schematic structure corresponding to one or more components of one or more of the proton beam emitting system 130, the first proton beam delivery system 140, and the second proton beam delivery system 142. The operational state component presentation 1112 can correspond to any component of any interlock of any of the proton beam emitting system 130, the first proton beam delivery system 140, and the second proton beam delivery system 142. The operational state component presentation 1112 can advantageously present a state of a component in real-time to a remote diagnostic system 600. As one example, the operational state component presentation 1112 can be a block, glyph, image, object, or the like corresponding to a generic or particular component.

The fault state component presentation 1114 includes a portion of the graphical user interface 1000 presenting a schematic structure corresponding to one or more components of one or more of the proton beam emitting system 130, the first proton beam delivery system 140, and the second proton beam delivery system 142, in a fault state. The fault state component presentation 1114 can correspond to any component of any interlock of any of the proton beam emitting system 130, the first proton beam delivery system 140, and the second proton beam delivery system 142. The fault state component presentation 1114 can advantageously present a fault state of a component in real-time to a remote diagnostic system 600 to further improve remote control and remote monitoring of the component directly. As one example, the fault state component presentation 1114 can be a block, glyph, image, object, coloration, or the like corresponding to a particular component and including a particular fault state block, glyph, image, object, coloration, or the like.

The component control interface 1120 includes a portion of the graphical user interface 1100 presenting one or more control affordances for modifying operating states of one or interlocks or components of one or more of the proton beam emitting system 130, the first proton beam delivery system 140, and the second proton beam delivery system 142. The component control interface 1120 may include at least one of an interlock control power interface 1122, an interlock control latch interface 1124, and a component control power interface 1126.

The interlock control power interface 1122 includes at least one control affordance for modifying an operating state of at least one component associated therewith. As one example, the interlock control power interface 1122 can send a power on or power off instruction to all components included in the interlock. The interlock control latch interface 1124 includes at least one control affordance for modifying at least one latch state of at least one component associated therewith. A latch state may indicate that an interlock is in one or more of a fault state and is not authorized for use in a clinical treatment, procedure, operation, or the like. As one example, the interlock control latch interface 1124 can send an unlatch instruction to a particular component included in the interlock, subsequent to a selection of the interlock at the component-level schematic view presentation 1110 or the like. As another example, the interlock control latch interface 1124 can send an unlatch instruction to every component included in the interlock, subsequent to a selection of the interlock at the component-level schematic view presentation 1110 or the like. The component control power interface 1126 includes at least one control affordance for modifying an operating state of at least one component associated therewith. As one example, the component control power interface 1126 can send a power on or power off instruction to a particular component included in the interlock, subsequent to a selection of the interlock at the component-level schematic view presentation 1110 or the like.

The component status presentation 1130 includes a portion of the graphical user interface 1100 presenting one or more component states associated with at least one of the proton beam emitting system 130, the first proton beam delivery system 140, and the second proton beam delivery system 142. The component status presentation 1130 may present a flat or non-hierarchical list view of one or more components associated with at least one of the proton beam emitting system 130, the first proton beam delivery system 140, and the second proton beam delivery system 142. The component status presentation 1130 can advantageously present an intuitive and near-real-time component-level presentation directly obtained from interconnects for one or more interconnects to one or more of the proton beam delivery system 130, the first proton beam delivery system 140, and the second proton beam delivery system 142. The component status presentation 1130 may include at least one of an interlock status presentation 1132, an operating status presentation 1134, and a component state presentation 1136.

The interlock status presentation 1132 includes a portion of the graphical user interface 1100 presenting at least one operating state identifier associated with at least one interlock of the proton beam emitting system 130, the first proton beam delivery system 140, and the second proton beam delivery system 142. As one example, the interlock status presentation 1132 can present an operational state indicator where a component included in the interlock is in a fault state. The operating status presentation 1134 includes a portion of the graphical user interface 1100 presenting at least one operating state identifier associated with at least one interlock of the proton beam emitting system 130, the first proton beam delivery system 140, and the second proton beam delivery system 142. As one example, the interlock status presentation 1132 can present an operational state indicator where a fault state component does not cascade to an interlock fault state. As another example, the interlock status presentation 1132 can present a fault state indicator where a fault state component does cascade to an interlock fault state. Thus, the interlock status presentation 1132 and the operating status presentation 1134 can together indicate whether a component is in a fault state and whether the component in the fault state results in a fault state of the interlock. The component state presentation 1136 includes a portion of the graphical user interface 1100 presenting at least one operating state identifier associated with at least one component of the proton beam emitting system 130, the first proton beam delivery system 140, and the second proton beam delivery system 142. The component status presentation 1130 may present a flat or non-hierarchical list view of one or more components associated with at least one of the proton beam emitting system 130, the first proton beam delivery system 140, and the second proton beam delivery system 142.

FIG. 12 illustrates an example method of remote monitoring of a proton beam emitting and delivery system, in accordance with present implementations. At least one of the example system 100 and the diagnostic system 600 may perform method 1200 according to present implementations. In some implementations, the method 1200 begins at step 1210.

At step 1210, the example system obtains one or more operating states corresponding to one or more components of a particle system. Step 1210 may include step 1212. At step 1212, the example system obtains one or more operating states from one or more components located at a remote physical site. The method 1200 then continues to step 1220.

At step 1220, the example system associates one or more operating states with one or more corresponding operating indicators. The method 1200 then continues to step 1230.

At step 1230, the example system generates a component hierarchy corresponding to one or more components of the particle system. Step 1230 may include at least one of steps 1230 and 1232. At step 1232, the example system generates a component hierarchy corresponding to a physical arrangement of components of a particle system. At step 1234, the example system generates the component hierarchy including one or more corresponding operating indicators. The method 1200 then continues to step 1240.

At step 1240, the example system obtains at least one system interlock template associated with one or more of the components of the particle system. Step 1240 may include step 1242. At step 1242, the example system obtains at least one system interlock template including one or more fault tolerance criterion or criteria associated with one or more corresponding components of the particle system. The method 1200 then continues to step 1250.

At step 1250, the example system identifies at least one faulted physical component from among the components of the particle system. Step 1250 may include at least one of steps 1252 and 1254. At step 1252, the example system identifies at least one device corresponding to the faulted physical component. At step 1254, the example system identifies a device corresponding to the faulted physical component based on at least one fault tolerance criterion associated with the device. The method 1200 then continues to step 1302.

Figure 13:
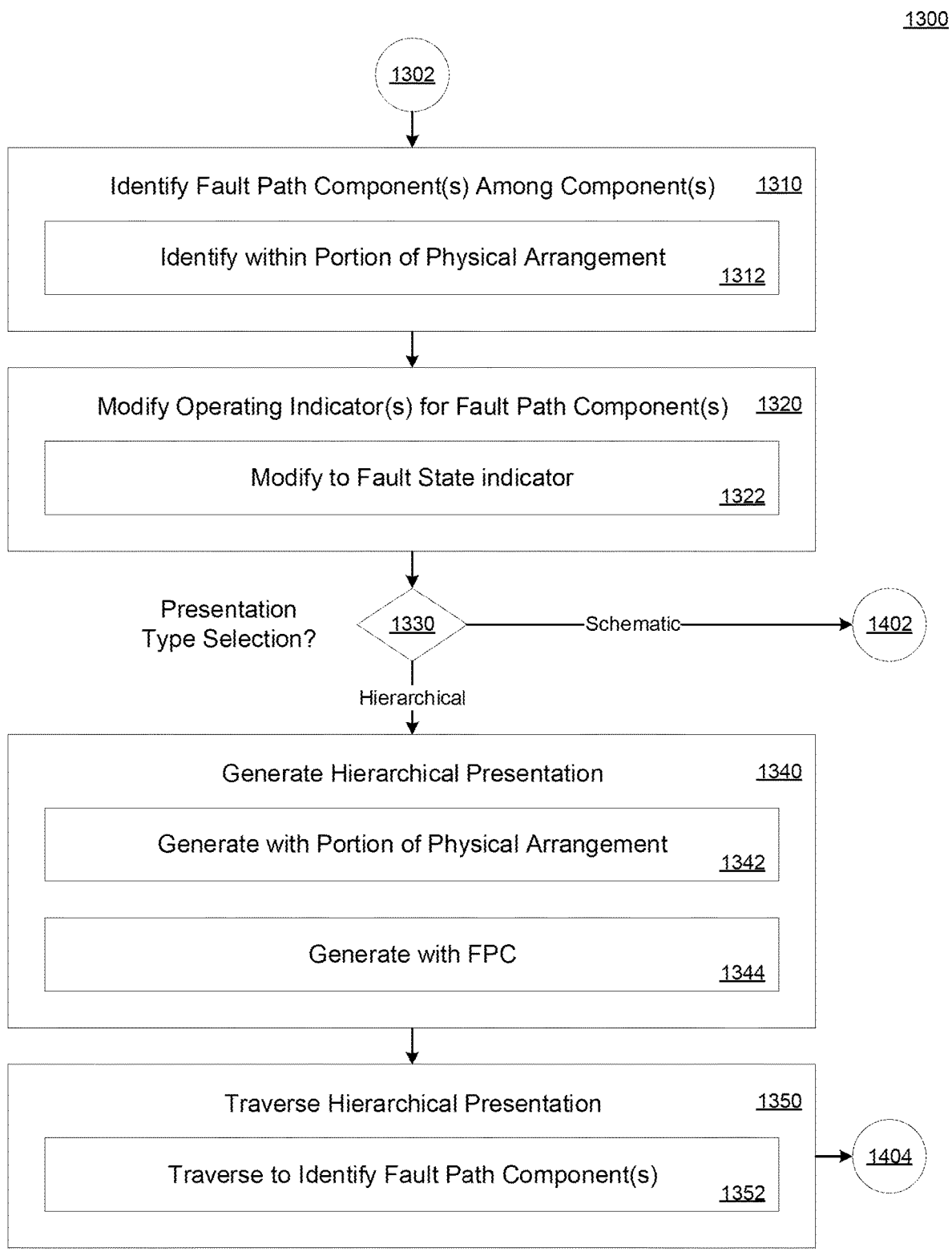
FIG. 13 illustrates a method of remote monitoring of a proton beam emitting and delivery system further to the method of FIG. 12, according to an embodiment.

FIG. 13 illustrates an example method of remote monitoring of a proton beam emitting and delivery system further to the example method of FIG. 12. At least one of the example system 100 and the diagnostic system 600 may perform method 1300 according to present implementations. The method 1300 may begin at step 1302. The method 1300 then continues to step 1310.

At step 1310, the example system identifies one or more fault path component among the components of the particle system. Step 1310 may include step 1312. At step 1312, the example system identifies one or more fault path components within a portion of a physical arrangement of one or more devices or components of the particle system. The method 1300 then continues to step 1320.

At step 1320, the example system modifies one or more operating indicators corresponding to one more fault path components. Step 1320 may include step 1322. At step 1322, the example system modifies one or more operating indicators to a fault state indicator. The method 1300 then continues to step 1330.

At step 1330, the example system determines whether a hierarchical or a schematic presentation type is selected. In accordance with a determination that a hierarchical presentation type is selected, the method 1300 continues to step 1340. In accordance with a determination that a schematic presentation type is selected, the method 1300 continues to step 1402. The example system can determine whether a hierarchical or a schematic presentation type is selected with respect to at least a portion of a presentation at a display. The example system can determine to present a hierarchical presentation at a first portion of a presentation and a schematic presentation at a second portion of the presentation concurrently, simultaneously, independently, or the like.

At step 1340, the example system generates a hierarchical presentation. Step 1340 may include at least one of steps 1342 and 1344. At step 1342, the example system generates a hierarchical presentation corresponding to a physical arrangement of one or more devices or components of a particle system. At step 1344, the example system generates a hierarchical presentation including at least one faulted physical components. The method 1300 then continues to step 1350.

At step 1350, the example system traverses a hierarchical presentation. Step 1350 may include step 1352. At step 1352, the example system traverses a hierarchical presentation to identify one or more fault path components. The method 1300 then continues to step 1404.

Figure 14:
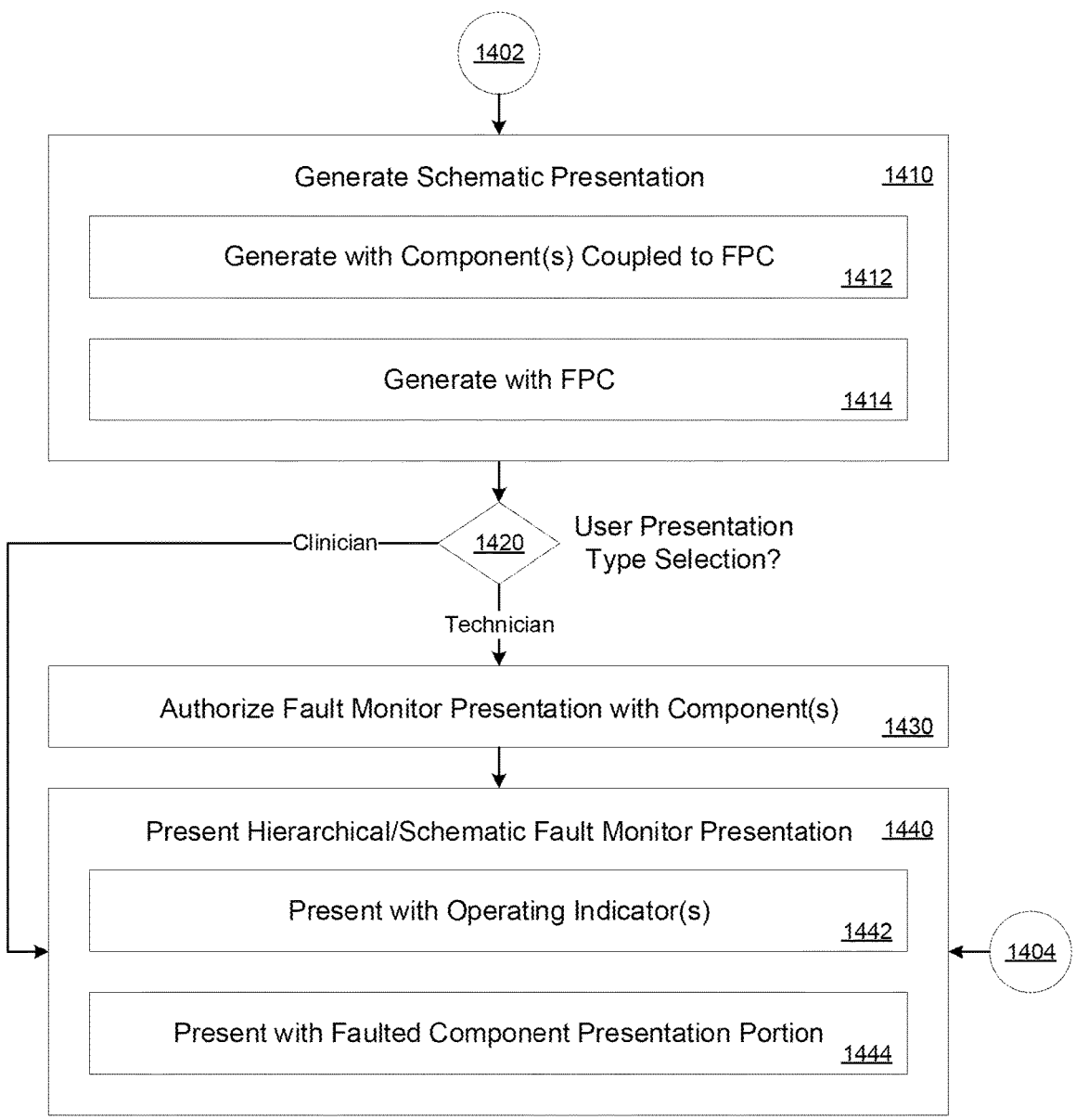
FIG. 14 illustrates a remote monitoring of a proton beam emitting and delivery system further to the method of FIG. 13, according to an embodiment.

FIG. 14 illustrates an example remote monitoring of a proton beam emitting and delivery system further to the example method of FIG. 13. At least one of the example system 100 and the diagnostic system 600 may perform method 1400 according to present implementations. In some implementations, the method 1400 begins at step 1402. The method 1400 then continues to step 1410.

At step 1410, the example system generates at least one schematic presentation. Step 1410 may include at least one of steps 1412 and 1414. At step 1412, the example system generates at least one schematic presentation including one or more components operatively coupled to at least one faulted physical component. At step 141, the example system generates at least one schematic presentation including one or more fault path components operatively coupled to at least one faulted physical component. The method 1400 then continues to step 1420.

At step 1420, the example system determines whether a user presentation type corresponds to a technician presentation or a clinician presentation. In accordance with a determination that a user presentation type corresponds to a technician presentation, the method 1400 continues to step 1430. Alternatively, in accordance with a determination that a user presentation type corresponds to a clinician presentation, the method 1400 continues to step 1440.

At step 1430, the example system authorizes a fault monitor presentation including presentation of one or more components of a particle system in one or more of a hierarchical presentation and a schematic presentation. The method 1400 then continues to step 1440.

At step 1440, the example system presents at least one of a hierarchical fault monitor presentation and a schematic fault monitor presentation. Step 1440 may include at least one of steps 1442 and 1444. At step 1442, the example system presents at least one fault monitor presentation including one or more operating indicators. At step 1444, the example system presents at least one fault monitor presentation including at least one faulted component presentation portion. The method 1400 may end at step 1440.

FIG. 15 illustrates an example method of remote control of a proton beam emitting and delivery system, in accordance with present implementations. At least one of the example system 100 and the diagnostic system 600 may perform method 1500 according to present implementations. The method 1500 may begin at step 1510.

At step 1510, the example system generates one or more operating state indicators corresponding to one or more operating states associated with one or more corresponding components of a particle system. The method 1500 then continues to step 1520.

At step 1520, the example system presents at least one fault control interface including at least one control affordance. Step 1520 may include at least one of steps 1522 and 1524. At step 1522, the example system presents at least one control affordance corresponding to at least one component of a particle system. At step 1524, the example system presents at least one fault control interface including at least one corresponding faulted component presentation portion. The method 1500 then continues to step 1530.

At step 1530, the example system presents at least one arrangement presentation including one or more components. Step 1530 may include at least one of steps 1532, 1534 and 1536. At step 1532, the example system presents at least one arrangement presentation including at least one interlock associated with one or more components of the particle system. At step 1534, the example system presents at least one arrangement presentation including at least one operating state indicator corresponding to one or more components of the particle system. At step 1536, the example system presents at least one arrangement presentation including at least one operating state indicator corresponding to at least one interlock corresponding to one or more components of the particle system. The method 1500 then continues to step 1540.

At step 1540, the example system polls for at least one control authorization instruction. Step 1540 may include step 1542. At step 1542, the example system polls a remote clinical site for at least one control authorization instruction. The method 1500 then continues to step 1550.

At step 1550, the example system receives at least one control affordance activation indication. The method 1500 then continues to step 1560.

At step 1560, the example system generates at least one device command corresponding to at least one component corresponding to a control affordance. The method 1500 then continues to step 1602.

Figure 16:
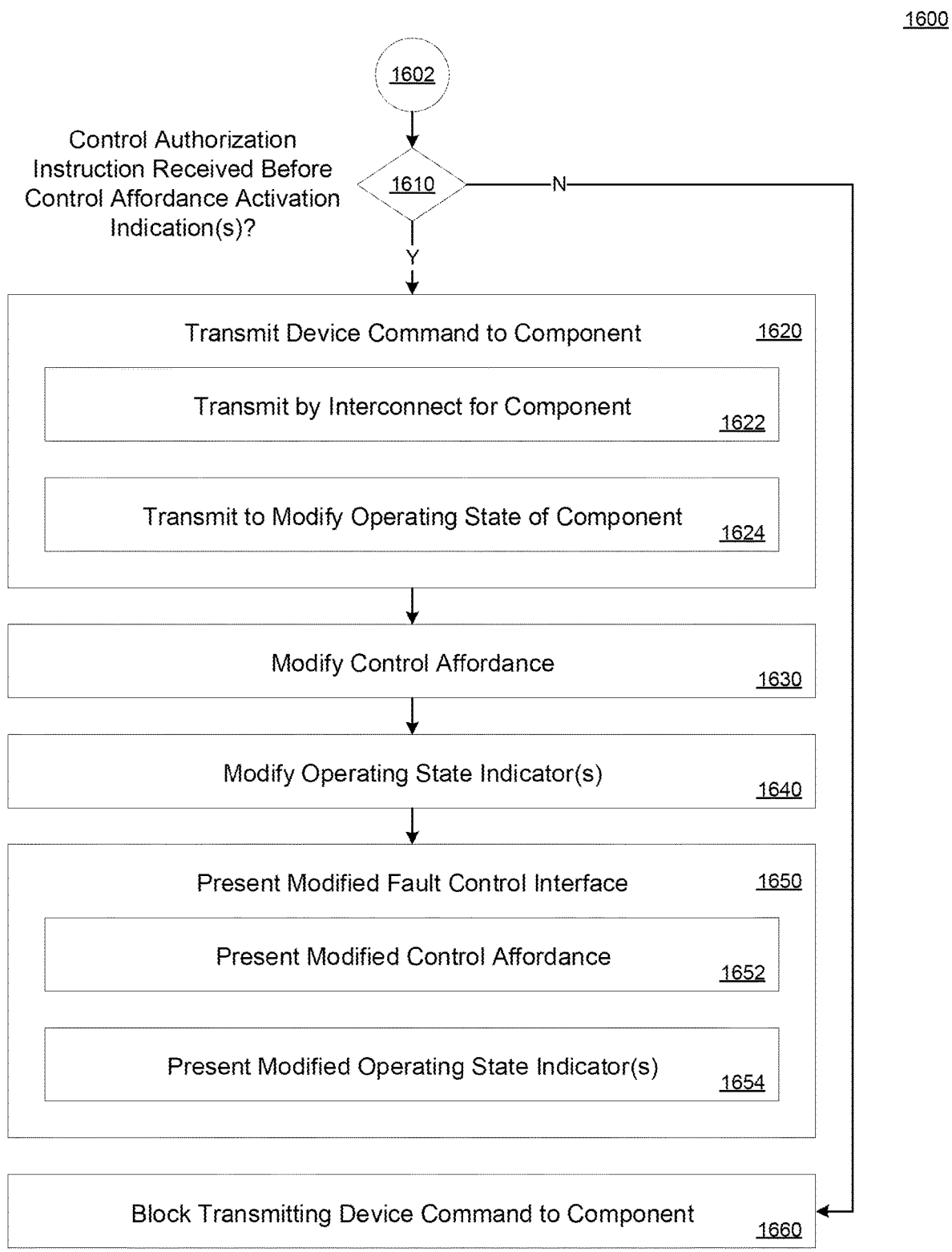
FIG. 16 illustrates a method of remote control of a proton beam emitting and delivery system further to the method of FIG. 15, according to an embodiment.

FIG. 16 illustrates an example method of remote control of a proton beam emitting and delivery system further to the example method of FIG. 15. At least one of the example system 100 and the diagnostic system 600 may perform method 1600 according to present implementations. The method 1600 may begin at step 1602. The method 1600 then continues to step 1610.

At step 1610, the example system determines whether a control authorization instruction is received before a control affordance activation instruction is received. In accordance with a determination that a control authorization instruction is received before a control affordance activation instruction is received, the method 1600 continues to step 1620. Alternatively, in accordance with a determination that a control authorization instruction is not received before a control affordance activation instruction is received, the method 1600 continues to step 1660.

At step 1620, the example system transmits at least one device command to at least one corresponding component. Step 1620 may include at least one of steps 1622 and 1624. At step 1622, the example system transmits at least one device command by at least one interconnect corresponding to the component. At step 1624, the example system transmits at least one device command to modify at least one operating state corresponding to the component. The method 1600 then continues to step 1630.

At step 1630, the example system modifies at least one control affordance. The example system may modify the control affordance in response to a user interaction to execute an operation by the control affordance. The method 1600 then continues to step 1640.

At step 1640, the example system modifies at least one operating state indicator. In some implementations, the example system modifies at least one operating state indicator corresponding to a component of the particle system. The method 1600 then continues to step 1650.

At step 1650, the example system presents at least one modified fault state control interface. Step 1650 may include at least one of steps 1652 and 1654. At step 1652, the example system presents at least one modified control affordance corresponding to the component associated with the modified operating state indicator. At step 1654, the example system presents one or more modified operating state indicators corresponding to the modified control affordance. The method 1600 then continues to step 1660.

At step 1660, the example system blocks transmitting of at least one device command to at least one component corresponding to the device command. The method 1600 may end at step 1660.

Figure 17:
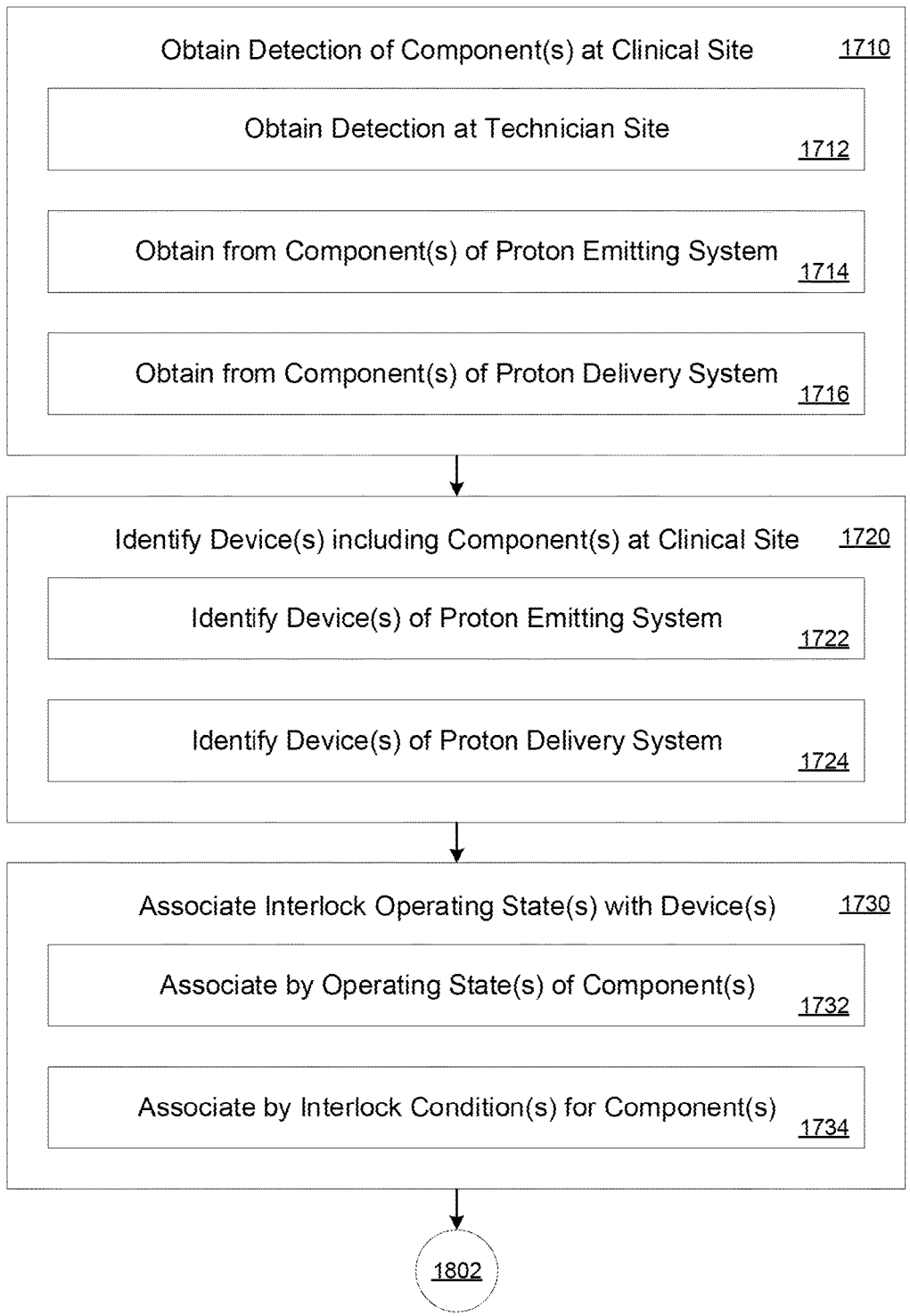
FIG. 17 illustrates a method of remote control of a proton beam emitting and delivery system at a service location, according to an embodiment.

FIG. 17 illustrates an example method of remote control of a proton beam emitting and delivery system at a service location, in accordance with present implementations. At least one of the example system 100 and the diagnostic system 600 may perform method 1700 according to present implementations. The method 1700 may begin at step 1710.

At step 1710, the example system obtains at least one detection of at least one component at a clinical site. A site can be a particular physical location or collection of physical locations. Step 1710 may include at least one of steps 1712, 1714 and 1716. At step 1712, the example system obtains at least one detection at a technician site remote from the clinical site. At step 1714, the example system obtains at least one detection from at least one component of a proton emitting system. At step 1716, the example system obtains at least one detection from at least one component of a proton delivery system. The method 1700 then continues to step 1720.

At step 1720, the example system identifies at least one device including at least one component at the clinical site. A device can be or correspond to an interlock associated with the group. Step 1720 may include at least one of steps 1722 and 1724. At step 1722, the example system identifies one or more devices of the proton emitting system. At step 1724, the example system identifies one or more devices of the proton delivery system. The method 1700 then continues to step 1730.

At step 1730, the example system associates at least one interlock operating state with at least one corresponding device. Step 1730 may include at least one of steps 1732 and 1734. At step 1732, the example system associates at least one interlock operating state with at least one corresponding device by at least one operating state associated with at least one of the components. At step 1734, the example system associates at least one interlock operating state with at least one corresponding device by at least one interlock condition associated with at least one of the components. The method 1700 then continues to step 1802.

Figure 18:
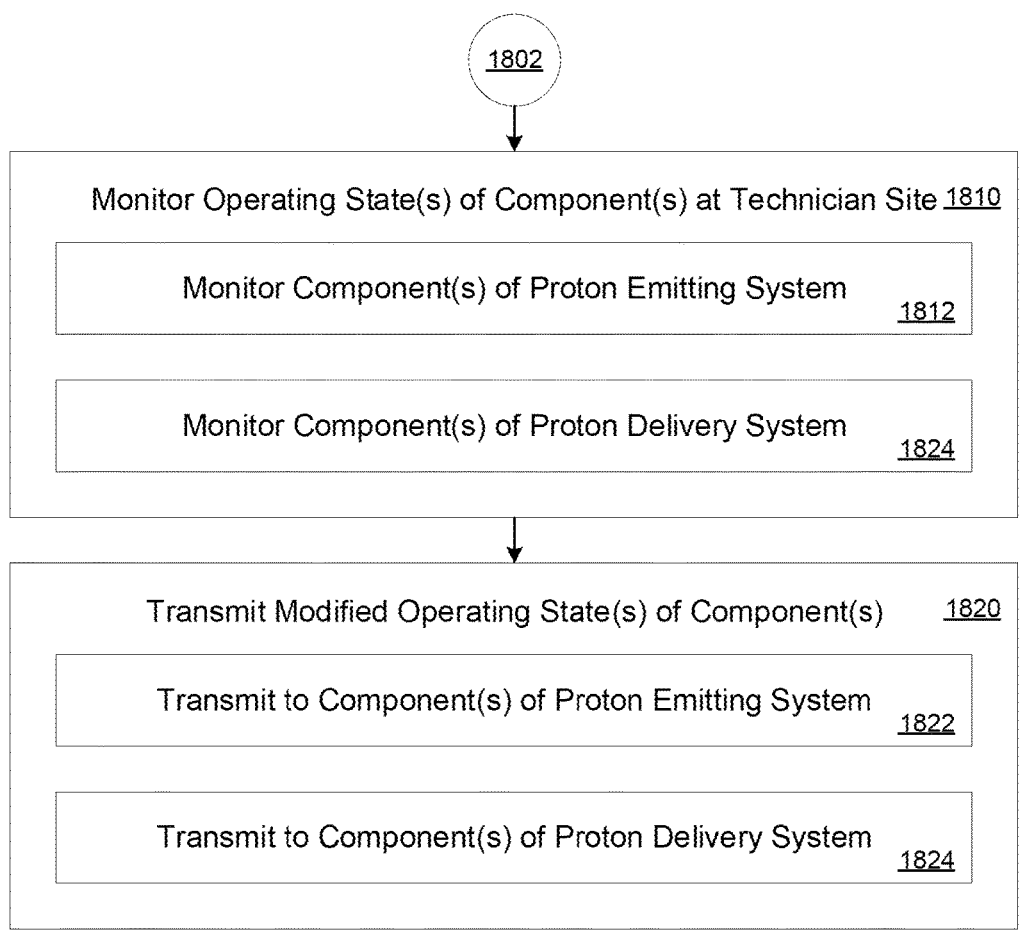
FIG. 18 illustrates a method of remote control of a proton beam emitting and delivery system at a service location, further to the method of FIG. 17, according to an embodiment.

FIG. 18 illustrates an example method of remote control of a proton beam emitting and delivery system at a service location, further to the example method of FIG. 17. At least one of the example system 100 and the diagnostic system 600 may perform method 1800 according to present implementations. The method 1800 may begin at step 1802. The method 1800 then continues to step 1810.

At step 1810, the example system monitors at least one operating state associated with at least one component at the technician site. Step 1810 may include at least one of steps 18112 and 1814. At step 1812, the example system monitors one or more components of a proton emitting system. At step 1814, the example system monitors one or more components of a proton delivery system. The method 1800 then continues to step 1820.

At step 1820, the example system transmits one or more modified operating states corresponding to one or more components. Step 1820 may include at least one of steps 1822 and 1824. At step 1822, the example system transmits one or more modified operating states to one or more corresponding components of a proton emitting system. At step 1824, the example system transmits one or more modified operating states to one or more corresponding components of a proton delivery system. The method 1800 may end at step 1820.

FIG. 19 illustrates an example method of remote control of a proton beam emitting and delivery system at a clinical location, in accordance with present implementations. At least one of the example system 100 and the proton beam system gateway 200 may perform method 1900 according to present implementations. The method 1900 may begin at step 1910.

At step 1910, the example system initializes one or more components at a clinical site. Step 1910 may include at least one of steps 1912, 1914 and 1916. At step 1912, the example system initializes one or more components of a proton beam emitting system. At step 1914, the example system one or more components of a proton beam delivery system. At step 1916, the example system initializes one or more components of a proton beam gateway system. The method 1900 then continues to step 1920.

At step 1920, the example system detects one or components at a clinical site. In some implementations, step 1920 includes at least one of steps 1922, 1924 and 1926. At step 1922, the example system detects one or components at a clinical site remote from a technician site. At step 1924, the example system detects one or components of a proton beam emitting system. At step 1926, the example system detects one or components of a proton beam delivery system. The method 1900 then continues to step 1930.

At step 1930, the example system interrogates one or more components for one or more corresponding operating states associated with the components. In some implementations, step 1930 includes at least one of steps 1932 and 1934. At step 1932, the example system interrogates one or more components corresponding to one or more components of a proton beam emitting system. At step 1934, the example system interrogates one or more components corresponding to one or more components of a proton beam emitting system. The method 1900 then continues to step 2002.

Figure 20:
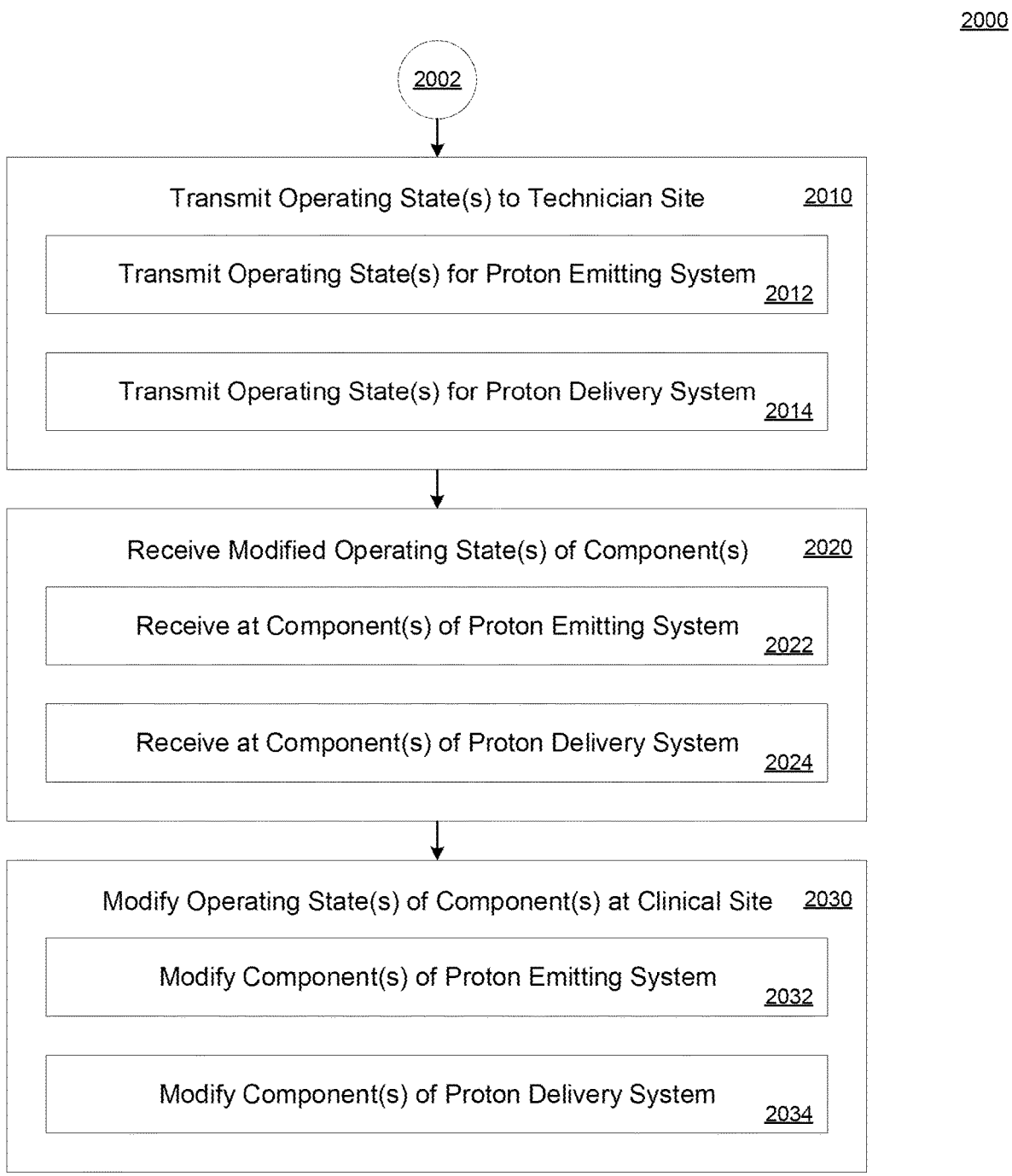
FIG. 20 illustrates a method of remote control of a proton beam emitting and delivery system at a clinical location, further to the method of FIG. 19, according to an embodiment.

FIG. 20 illustrates an example method of remote control of a proton beam emitting and delivery system at a clinical location, further to the example method of FIG. 19. At least one of the example system 100 and the proton beam system gateway 200 may perform method 2000 according to present implementations. The method 2000 may begin at step 2002. The method 2000 then continues to step 2010.

At step 2010, the example system transmits one or more operating states to a technician site. Step 2010 may include at least one of steps 2012 and 2014. At step 2012, the example system transmits one or more operating states associated with a proton emitting system. At step 2014, the example system transmits one or more operating states associated with a proton delivery system. The method 2000 then continues to step 2020.

At step 2020, the example system receives one or more modified operating states for one or more components. Step 2020 may include at least one of steps 2022 and 2024. At step 2022, the example system receives one or more modified operating states at one or more components of a proton emitting system. At step 2024, the example system receives one or more modified operating states at one or more components of a proton delivery system. The method 2000 then continues to step 2030.

At step 2030, the example system modifies one or more operating states for one or more components at a clinical site. Step 2030 may include at least one of steps 2032 and 2034. At step 2032, the example system modifies one or more component of a proton emitting system. At step 2034, the example system modifies one or more component of a proton emitting system. In some implementations, the method 2000 ends at step 2030.

The herein described subject matter sometimes illustrates different components contained within, or connected with, different other components. It is to be understood that such depicted architectures are illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Further, unless otherwise noted, the use of the words "approximate," "about," "around," "substantially," etc., mean plus or minus ten percent.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. It is intended that the scope of the invention be defined by the claims appended hereto and their equivalents.

What is claimed is:

1. A method for remote diagnostic monitoring of operating states for physical components of a particle accelerator system, the method comprising:
    generating, by at least one processor, a component hierarchy corresponding to a physical arrangement of one or more physical components of a particle emitting system and including corresponding operating indicators of operating states of the physical components;
    identifying, by the at least one processor, a faulted physical component among the physical components;
    identifying, by the at least one processor, one or more fault path components among the physical components, the fault path components corresponding to a portion of the physical arrangement associated with the faulted physical component; and
    modifying, by the at least one processor, the operating indicators of the fault path components to fault state indicators; and
    instructing a graphical user interface to present a faulted component presentation portion corresponding to the component hierarchy and including the fault state indicators of one or more of the fault path components and of the faulted physical component.

2. The method of claim 1, further comprising:
    generating one or more of a hierarchical presentation including at least the portion of the physical arrangement associated with the faulted physical component, and a schematic presentation including at least the faulted physical component and at least one physical component operatively coupled to the faulted physical component.

3. The method of claim 2, wherein the physical arrangement corresponds to at least one physical device comprising at least one included physical component among the physical components, and the hierarchical presentation includes at least one of the physical device and the included physical component in accordance with a monitor access criterion.

4. The method of claim 3, wherein the monitor access criterion corresponds to a first access criterion, and the hierarchical presentation includes the physical device and the included physical component.

5. The method of claim 3, wherein the monitor access criterion corresponds to a second access criterion, and the hierarchical presentation includes the physical device and excludes the included physical component.

6. The method of claim 3, wherein the identifying the faulted physical component comprises identifying the included physical component, and the identifying the fault path components among the physical components comprises identifying the physical device.

7. The method of claim 6, wherein the identifying the physical device comprises identifying the physical device in accordance with a fault tolerance criterion associated with the physical device and the included physical component.

8. The method of claim 7, further comprising:
    obtaining, by the at least one processor, a system interlock template corresponding to the physical components associated with one or more of the particle emitting system and the particle delivery system,
    wherein the system interlock template includes the fault tolerance criterion.

9. The method of claim 2, further comprising:
    traversing, by the at least one processor, the hierarchical presentation in accordance with the component hierarchy to identify the faulted physical component and one or more of the fault path components.

10. The method of claim 1, further comprising:
    presenting, by the at least one processor, a fault monitor presentation including the operating indicators and a faulted component presentation portion corresponding to the fault state indicators,
    wherein the at least one processor located at a first physical location and the physical components located at a second physical location remote from the first physical location.

11. A user interface system for remote diagnostic monitoring of operating states for physical components of a particle system, the system comprising:
    a hierarchy processing engine configured to generate a component hierarchy corresponding to a physical arrangement of one or more physical components associated with a particle emitting system and a particle delivery system and including corresponding operating indicators of operating states of one or more of the particle emitting system and a particle delivery system, identify one or more fault path components among the physical components, the fault path components corresponding to a portion of the physical arrangement associated with the faulted physical component, and modify the operating indicators of the fault path components to fault state indicators; and
    a presentation engine configured to present, via a graphical user interface, a fault monitor presentation including the operating indicators and a faulted component presentation portion corresponding to the component hierarchy and including the fault state indicators of one or more of the fault path components and of the faulted physical component.

12. The system of claim 11, wherein the presentation engine comprises:
a hierarchy presentation engine configured to generate a hierarchical presentation including at least the portion of the physical arrangement associated with the faulted physical component,
wherein the fault monitor presentation comprises the hierarchical presentation.

13. The system of claim 12, wherein the physical arrangement corresponds to at least one physical device comprising at least one included physical component among the physical components, and the hierarchical presentation includes at least one of the physical device and the included physical component in accordance with a monitor access criterion.

14. The system of claim 13, wherein the presentation engine further comprises:
an interlock presentation controller configured to selectably present, in accordance with a first access criterion, the hierarchical presentation including the physical device and the included physical component, and to selectably present, in accordance with a second access criterion, the hierarchical presentation including the physical device and excluding the included physical component.

15. The system of claim 13, wherein the hierarchy processing engine is further configured to identify the faulted physical component by identifying the included physical component, and identify the fault path components among the physical components by identifying the physical device.

16. The system of claim 15, wherein the hierarchy processing engine is further configured to identify the physical device in accordance with a fault tolerance criterion associated with the physical device and the included physical component.

17. The system of claim 16, further comprising:
a network interface operatively coupled to the particle emitting system and the particle delivery system, and configured to obtain a system interlock template corresponding to the physical components associated with the particle emitting system and the particle delivery system,
wherein the system interlock template includes the fault tolerance criterion.

18. The system of claim 11, wherein the presentation engine comprises:
a schematic presentation engine configured to generate a schematic presentation including at least the faulted physical component and at least one physical component operatively coupled to the faulted physical component,
wherein the fault monitor presentation comprises the schematic presentation.

19. A computer system comprising:
a processor in communication by a network interface with physical components of a particle accelerator system, the processor configured to:
generate a component hierarchy corresponding a physical arrangement of one or more physical components of a particle emitting system and including corresponding operating indicators of operating states of the physical components;
identify a faulted physical component among the physical components;
identify one or more fault path components among the physical components, the fault path components corresponding to a portion of the physical arrangement associated with the faulted physical component;
modify the operating indicators of the fault path components to fault state indicators; and
instruct a graphical user interface to present a fault monitor presentation including the operating indicators and a faulted component presentation portion corresponding to the component hierarchy and including the fault state indicators of one or more of the fault path components and of the faulted physical component.

20. The system of claim 1, wherein the particle emitting system comprises a proton beam cyclotron.

* * * * *